(12) United States Patent
Smith et al.

(10) Patent No.: US 9,376,710 B2
(45) Date of Patent: *Jun. 28, 2016

(54) METHODS OF LOCALIZING NUCLEIC ACIDS TO ARRAYS

(71) Applicant: ILLUMINA CAMBRIDGE LIMITED, Walden, Essex (GB)

(72) Inventors: Mark Edward Brennan Smith, Walden (GB); Andrea Sabot, Walden (GB); Isabelle Marie Julia Rasolonjatovo, Walden (GB); Jean-Ernest Sohna Sohna, Cambridgeshire (GB); Adrian Martin Horgan, Walden (GB); Harold Philip Swerdlow, Walden (GB)

(73) Assignee: ILLUMINA CAMBRIDGE LTD., Little Chesterford, Essex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,766

(22) Filed: Jan. 8, 2015

(65) Prior Publication Data

US 2015/0119295 A1    Apr. 30, 2015

Related U.S. Application Data

(60) Continuation of application No. 14/053,333, filed on Oct. 14, 2013, now Pat. No. 8,969,258, which is a division of application No. 13/548,558, filed on Jul. 13, 2012, now Pat. No. 8,563,477, which is a continuation of application No. 10/585,373, filed as application No. PCT/GB2005/000033 on Jan. 7, 2005, now abandoned.

(30) Foreign Application Priority Data

Jan. 7, 2004  (GB) .................................. 0400253.1
Aug. 5, 2004  (EP) .................................. 04254726

(51) Int. Cl.
  C40B 50/18   (2006.01)
  C12Q 1/68    (2006.01)
  B01J 19/00   (2006.01)
  C40B 40/06   (2006.01)

(52) U.S. Cl.
  CPC .......... *C12Q 1/6806* (2013.01); *B01J 19/0046* (2013.01); *C12Q 1/6876* (2013.01); *C40B 40/06* (2013.01); *C40B 50/18* (2013.01); *B01J 2219/0061* (2013.01); *B01J 2219/0072* (2013.01); *B01J 2219/00527* (2013.01); *B01J 2219/00529* (2013.01); *B01J 2219/00605* (2013.01); *B01J 2219/00612* (2013.01); *B01J 2219/00617* (2013.01); *B01J 2219/00626* (2013.01); *B01J 2219/00637* (2013.01); *B01J 2219/00639* (2013.01); *B01J 2219/00641* (2013.01); *Y10T 428/265* (2015.01)

(58) Field of Classification Search
  None
  See application file for complete search history.

(56) References Cited

U.S. PATENT DOCUMENTS

| | | | |
|---|---|---|---|
| 5,212,253 A | 5/1993 | Ponticello et al. | |
| 5,302,509 A | 4/1994 | Cheeseman | |
| 5,654,413 A | 8/1997 | Brenner | |
| 5,858,653 A | 1/1999 | Duran et al. | |
| 5,948,621 A | 9/1999 | Turner et al. | |
| 6,077,674 A | 6/2000 | Schleifer et al. | |
| 6,221,635 B1 | 4/2001 | Rovera et al. | |
| 6,372,813 B1 | 4/2002 | Johnson et al. | |
| 6,465,178 B2 | 10/2002 | Chappa et al. | |
| 7,481,958 B2 | 1/2009 | Kawakami et al. | |
| 8,563,477 B2 * | 10/2013 | Smith ............................. 506/13 | |
| 8,969,258 B2 * | 3/2015 | Smith .................. B01J 19/0046 506/32 | |
| 2003/0008413 A1 | 1/2003 | Kim et al. | |
| 2003/0044389 A1 | 3/2003 | Brown et al. | |
| 2003/0157260 A1 | 8/2003 | Rubner et al. | |
| 2004/0248144 A1 | 12/2004 | Mir | |
| 2008/0280773 A1 | 11/2008 | Fedurco | |

FOREIGN PATENT DOCUMENTS

| | | |
|---|---|---|
| WO | WO 97/04131 | 2/1997 |
| WO | WO 98/44151 | 10/1998 |
| WO | WO 98/44152 | 10/1998 |
| WO | WO 99/61653 | 12/1999 |
| WO | WO 00/06770 | 2/2000 |
| WO | WO 00/18957 | 4/2000 |
| WO | WO 00/31148 | 6/2000 |
| WO | WO 00/53812 | 9/2000 |
| WO | WO 01/01143 | 1/2001 |
| WO | WO 01/62982 | 8/2001 |
| WO | WO 01/66554 | 9/2001 |
| WO | WO 02/12566 | 2/2002 |
| WO | WO 01/23082 | 4/2002 |
| WO | WO 02/059372 | 8/2002 |
| WO | WO 03/014392 | 2/2003 |

(Continued)

OTHER PUBLICATIONS

"Notice of Reasons for Rejection (English Translation), Mailed Nov. 9, 2010, in Japanese Application 2006-548380 (From PCT/GB2005/000033, The Present Application), Citing Japanese Laid-Open No. 2003-525945."
Adessi C. et al. (2000) Nucl. Acids Res. 28(20), e87.
Andreadis J. D. et al. (2000) Nucl. Acids Res. 28(2), e5.
Binnig et al., *Helvetica Physi ca Acta* (1982) 55:726-735.
Braslavsky, I. et al., *Proct Nat. Acad. Sci* (Apr. 1, 2003), 100 (7), 3960-3964.
Efimov et al. (*Nucleic Acids Research*, 1999, 27 (22), 4416-4426.
Fodor et al., *Trends in Biotechnology* (1994) 12:19-26.
Guo, Z. et al (1994) Nucl. Acids Res. 22, 5456-5465.
Hansma et al., *Ann. Rev. Biophys. Biomol. Struct.* (1994) 23:115-139.
Huber M. et al. (2001) Anal. Biochem. 299(1), 24-30.

(Continued)

*Primary Examiner* — Lianko Garyu

(74) *Attorney, Agent, or Firm* — Knobbe, Martens, Olson & Bear LLP

(57) ABSTRACT

Methods and compositions are disclosed relating to the localization of nucleic acids to arrays such as silane-free arrays, and of sequencing the nucleic acids localized thereby.

20 Claims, 12 Drawing Sheets

(56) References Cited

FOREIGN PATENT DOCUMENTS

| WO | WO 03/014394 | 2/2003 |
| WO | WO 03/074734 | 9/2003 |
| WO | WO 2004/073843 | 9/2004 |
| WO | WO 2005/047301 | 5/2005 |
| WO | WO 2006-064199 | 6/2006 |

OTHER PUBLICATIONS

Kartalov, E.P. et al., *Biotechniques* (Mar. 2003), 34: 505-510.
Mitra, R. D. et al. (1999) Nucl. Acids Res. 27(24), e34.
Moyer et al., *Laser Focus World* (1993) 29 (10).
Patani, et al., "Bioisoterism: A Rational Approach in Drug Design", Chemical Reviews, 96, 1996, 3147-3176.
Peterson, A.W. et al. (2001) Nucl. Acids Res. 29, 5163-5168.
Pirrung et al. *Langmuir*, 2000, 16, 2185-2191.
Sambrook et al., 2001, *Molecular Cloning, A Laboratory Manual*, 3rd Ed, Cold Spring Harbor Laboratory Press, Cold Spring Harbor Laboratory Press, NY.
Schena et al., *Science* (1995) 270:467-470.
Shapero M. H. et al. (2001) Genome Res. 11,1926-1934.
Shchepinov, M.S. et al. "*Steric factors influencing hybridization of nucleic acids to oligonucleotide arrays*" (1997) Nucl. Acids Res. 25, 1155-1161.
Sjoroos M. et al. (2001) Clin. Chem. 47(3), 498-504.
Stamm S. et al. (1991) Nucl. Acids Res. 19(6), 1350.
Vale et al., *Nature* (1996) 380:451-453.
Weiler, J et al. (1997) Nucl. Acids Res. 25, No. 14, 2792-2799.
Zhao et al. (*Nucleic Acids Research*, 2001, 29(4), 955-959.

\* cited by examiner

METHODS OF LOCALIZING NUCLEIC ACIDS TO ARRAYS

CROSS REFERENCE TO RELATED APPLICATION

This application is a continuation of U.S. application Ser. No. 14/053,333 filed Oct. 14, 2013 which is a divisional of U.S. application Ser. No. 13/548,558, filed Jul. 13, 2012, issuing as U.S. Pat. No. 8,563,477 on Oct. 22, 2013, which is a continuation of U.S. application Ser. No. 10/585,373, which is a National Stage Application claiming the priority of PCT Application No. PCT/GB2005/000033 filed on Jan. 7, 2005, which in turn claims priority from Great Britain Application Serial No. 0400253.1 filed on Jan. 7, 2004 and European Application Serial No. 04254726.5 filed on Aug. 5, 2004, the entire disclosures of each of which are incorporated herein by reference.

SEQUENCE LISTING

The present application includes a sequence listing in Electronic format. The Sequence Listing is provided as a file entitled ILLINC214C2SEQLIST.TXT, created Jan. 8, 2015, which is approximately 4 kb in size. The information in the electronic format of the sequence listing is incorporated herein by reference in its entirety.

BACKGROUND OF THE INVENTION

1. Field of the Invention

This invention relates to the construction of arrays of molecules. In particular, the invention relates to the preparation of a hydrogel surface useful in the formation and manipulation of arrays of molecules, particularly polynucleotides and to the chemical modification of these and other arrays.

2. Description of the Related Art

Advances in the study of molecules have been led, in part, by improvement in technologies used to characterize the molecules or their biological reactions. In particular, the study of nucleic acids, such as DNA and RNA, and other large biological molecules, such as proteins, has benefited from developing technologies used for sequence analysis and the study of hybridisation events.

An example of the technologies that have improved the study of nucleic acids is the development of fabricated arrays of immobilised nucleic acids. These arrays typically consist of a high-density matrix of polynucleotides immobilised onto a solid support material. Fodor et al., *Trends in Biotechnology* (1994) 12:19-26, describe ways of assembling the nucleic acid arrays using a chemically sensitised glass surface protected by a mask, but exposed at defined areas to allow attachment of suitably modified nucleotides. Typically, these arrays may be described as "many molecule" arrays, as distinct regions are formed on the solid support comprising a high density of one specific type of polynucleotide.

An alternative approach is described by Schena et al., *Science* (1995) 270:467-470, where samples of DNA are positioned at predetermined sites on a glass, microscope slide by robotic micropipetting techniques.

A further development in array technology is the attachment of the polynucleotides to a solid support material to form single molecule arrays (SMAs). Arrays of this type are disclosed in WO00/06770. The advantage of these arrays is that reactions can be monitored at the single molecule level and information on large numbers of single molecules can be collated from a single reaction.

Although these arrays offer particular advantages in sequencing experiments, the preparation of arrays at the single molecule level is more difficult than at the multi-molecule level, where losses of target polynucleotide can be tolerated due to the multiplicity of the array. Moreover, where the sequence of a polynucleotide is determined by sequential incorporations of labelled nucleotides, a further problem which arises is the occurrence of non-specific binding of nucleotides to the array, for example to the surface of the array. There is, therefore, a constant need for improvements in the preparation of arrays of molecules, particularly polynucleotides, for example single molecule arrays of polynucleotides, for sequencing procedures.

Solid-supported molecular arrays have been generated previously in a variety of ways. Indeed, the attachment of biomolecules (such as proteins and nucleic acids, e.g. DNA) to a variety of supports/substrates (e.g. silica-based substrates such as glass or plastics or metals) underpins modern microarray and biosensor technologies employed for genotyping, gene expression analysis and biological detection.

In nearly all examples where biomolecules have been immobilised on solid supports, the attachment chemistry is designed around the support. For example, silanes (e.g. functionalised silanes such as chloro- or alkoxy-silanes) are commonly used to modify glass; thiols are often used to modify the surface of gold. A potential problem here is that the agents used to modify one surface are often unsuitable for modifying the surface of another support. For example, thiols cannot be used to modify glass, nor can silanes be used to modify gold.

Silica-based substrates such as silica or glass are often employed as supports on which molecular arrays are constructed. It would be desirable to be able to use chemistry useful in modifying such supports with other supports.

Prior to the construction of any silica-based solid-supported arrays, the support surface is generally thoroughly cleaned. With silica-based substrates, the resultant cleaned surface possesses hydroxyl groups which are either neutral and/or deprotonated and thus negatively charged. As a result there is a degree of resistance to non-specific binding of nucleotides used in sequencing experiments. Either the neutral hydroxyl groups do not attract the negatively charged nucleotides, or the deprotonated groups' negative charge serves to repel the nucleotides. Regardless, the effect of the surface towards the non-specific, and undesired, binding of nucleotides is not high and it is desirable to lessen the extent of non-specific binding in sequencing experiments. This serves to reduce background "noise" during the detection of each individual nucleotide in each step in sequencing experiments.

Another way in which polynucleotides (and other molecules) have been displayed previously on the surface of solid support is through the use of hydrogels. Molecular arrays, e.g. microarrays, of molecules, particularly polynucleotides, are of use in techniques including nucleic acid amplification and sequencing methods. In preparing hydrogel-based solid-supported molecular arrays, a hydrogel is formed and molecules displayed from it. These two features—formation of the hydrogel and construction of the array—may be effected sequentially or simultaneously.

Where the hydrogel is formed prior to formation of the array, it is typically produced by allowing a mixture of comonomers to polymerise. Generally, the mixture of comonomers contain acrylamide and one or more comonomers, the latter of which permit, in part, subsequent immobilisation of molecules of interest so as to form the molecular array.

The comonomers used to create the hydrogel typically contain a functionality that serves to participate in crosslinking of the hydrogel and/or immobilise the hydrogel to the solid support and facilitate association with the target molecules of interest.

Generally, as is known in the art, polyacrylamide hydrogels are produced as thin sheets upon polymerisation of aqueous solutions of acrylamide solution. A multiply unsaturated (polyunsaturated) crosslinking agent (such as bisacrylamide) is generally present; the ratio of acrylamide to bisacrylamide is generally about 19:1. Such casting methods are well known in the art (see for example Sambrook et al., 2001, *Molecular Cloning, A Laboratory Manual*, 3$^{rd}$ Ed., Cold Spring Harbor Laboratory Press, Cold Spring Harbor Laboratory Press, NY) and need not be discussed in detail here.

As an alternative to the use of hydrogel-supported molecular arrays, the use of polyelectrolyte multilayers (PEMs) has been reported (E. P. Kartov et al., *Biotechniques* (March 2003), 34:505-510; and I. Braslaysky et al., *Proct Nat. Acad. Sci* (1 Apr. 2003), 100 (7), 3960-3964} to allow sequencing experiments to be conducted in which fluorescently labelled molecules are incorporated into DNA strands and then identified by fluorescence microscopy. The authors report that, by using PEMs, the charge density on the surface may be tuned so as to repel labelled nucleotides selectively by constructing the PEMs such that the final layer bears a negative charge.

Accordingly, the authors describe such a PEM which, after its construction, was used in the formation of a molecular array. The latter was formed initially by biotinylating the surface using a commercially available kit (EZ-Link™ kit from Pierce Chemical (Rockford, Ill., USA)). The biotinylated PEM was then coated with Streptavidin-Plus™ (Prozyme, San Leandro, Calif., USA) to which biotinylated DNA was attached. In this way the biotinylated DNA is attached to covalently bound biotin through specific noncovalent interactions to "sandwiched" streptavidin molecules.

The authors of B. P. Kartov et al. (infra) and I. Braslaysky et al. (two authors are common to both publications) report that the final, negatively charged, polyacrylic acid layer is intended to prevent negatively charged labelled nucleotides binding to the surface. It is clear, however, that this was not successful in every instance since it is reported in I. Braslaysky et al. (infra) that the identity of the third or fourth incorporated nucleotide could not be determined (was "ambiguous"). According to the authors, this was caused by "increasing non-specific binding of unincorporated nucleotides".

Accordingly, there exists a need for a method of providing arrays of molecules, particularly polynucleotides, which arrays have a lesser tendency to interact nonspecifically with other molecules (and in particular (optionally fluorescently labelled) nucleotides used in sequencing experiments) than those available in the prior art. There is also a need for a general method for modifying a solid support to allow the preparation of supports useful in the preparation of arrays.

SUMMARY OF THE INVENTION

Heretofore, some form of covalent surface modification of the solid support has been practised in order to achieve satisfactory immobilisation of either hydrogel-based molecular arrays or hydrogels to which it is desired to array molecules. Surprisingly, we have found that such functional modification of the support is not necessary in order to achieve satisfactory immobilisation of arrays of molecules of interest, in particular polynucleotides. In order to make useful supported arrays capable of binding molecules of interest, we have found that a mixture of comonomers comprising at least one hydrophilic monomer and a functionalised comonomer (functionalised to the extent that the monomer once incorporated into the polymer is capable of binding the molecule of interest to the surface of the hydrogel) may be polymerised so as to form a hydrogel capable of being immobilised on a solid supported, preferably a silica-based, substrate.

Viewed from one aspect, therefore, the invention provides a method of preparing a hydrogel immobilised to a solid support comprising polymerising on said support a mixture of:

(i) a first comonomer which is acrylamide, methacrylamide, hydroxyethyl methacrylate or N-vinyl pyrrolidinone; and (ii) a second comonomer which is a functionalized acrylamide or acrylate of formula (I):

$$H_2C=C(H)-C(=O)\text{-A-B-C} \qquad (I);$$

or a methacrylate or methacrylamide of formula (II):

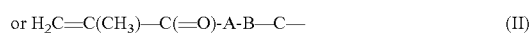

$$\text{or } H_2C=C(CH_3)-C(=O)\text{-A-B-C-} \qquad (II)$$

(wherein:

A is NR or O, wherein R is hydrogen or an optionally substituted saturated hydrocarbyl group comprising 1 to 5 carbon atoms;

—B— is an optionally substituted alkylene biradical of formula —(CH$_2$)$_n$— wherein n is an integer from 1 to 50; and wherein n=2 or more, one or more optionally substituted ethylene biradicals —CH$_2$CH$_2$— of said alkylene biradical may be independently replaced by ethenylene and ethynylene moieties; and wherein n=1 or more, one or more methylene biradicals —CH$_2$— may be replaced independently with an optionally substituted mono- or polycyclic hydrocarbon biradical comprising from 4 to 50 carbon atoms, or a corresponding heteromonocyclic or heteropolycyclic biradical wherein at least 1 CH$_2$ or CH$_2$ is substituted by an oxygen sulfur or nitrogen atom or an NH group; and C is a group for reaction with a compound to bind said compound covalently to said hydrogel) to form a polymerized product, characterised in that said method is conducted on, and immobilises the polymerised product to, said support which is not covalently surface-modified.

Viewed from a second aspect, the invention provides a solid-supported hydrogel obtainable according to the method of the first invention.

Viewed from a third aspect, the invention provides a method of preparing a solid-supported hydrogel-based molecular array by attaching one or more molecules of interest to reactive sites present in the solid-supported hydrogel according to the invention.

In a particular embodiment the invention provides a method of preparing a solid-supported hydrogel-based molecular array which is a clustered array by attaching oligonucleotide primers to reactive sites present in the solid-supported hydrogel and performing nucleic acid amplification of a template using the bound primers.

Viewed from a fourth aspect, the invention provides a solid-supported hydrogel-based molecular array obtainable according to the third aspect of the invention.

Viewed from a fifth aspect, the invention provides the use of a molecular array according to the fourth aspect of the invention in any method of analysis which requires interrogation of the molecules of interest or molecules bound thereto.

The use of solid-supported hydrogel arrays in single molecule array applications has not been conducted previously.

Thus viewed from a sixth aspect, the invention provides the use of solid-supported hydrogel arrays in single molecule array applications, preferably wherein said arrays are obtainable, and generally obtained, by a method comprising:

(1) preparing a hydrogel immobilised to a solid support comprising polymerising on said support a mixture of:

(i) a first comonomer which is acrylamide, methacrylamide, hydroxyethyl methacrylate or N-vinyl pyrrolidinone; and (ii) a second comonomer which is a functionalized acrylamide or acrylate of formula (I):

$$H_2C=C(H)-C(=O)-A-B-C \quad (I);$$

or a methacrylate or methacrylamide of formula (II):

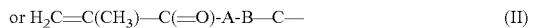

$$\text{or } H_2C=C(CH_3)-C(=O)-A-B-C- \quad (II)$$

(wherein:

A is NR or O, wherein R is hydrogen or an optionally substituted saturated hydrocarbyl group comprising 1 to 5 carbon atoms;

—B— is an optionally substituted alkylene biradical of formula —$(CH_2)_n$— wherein n is an integer from 1 to 50; and wherein n=2 or more, one or more optionally substituted ethylene biradicals —$CH_2CH_2$— of said alkylene biradical may be independently replaced by ethenylene and ethynylene moieties; and wherein n=1 or more, one or more methylene biradicals —$CH_2$— may be replaced independently with an optionally substituted mono- or polycyclic hydrocarbon biradical comprising from 4 to 50 carbon atoms, or a corresponding heteromonocyclic or heteropolycyclic biradical wherein at least 1 $CH_2$ or $CH_2$ is substituted by an oxygen sulfur or nitrogen atom or an NH group; and C is a group for reaction with a compound to bind said compound covalently to said hydrogel) to form a polymerized product, and (2) attaching one or more molecules of interest to reactive sites present in the hydrogel produced in step (1).

The invention also provides the use of, and methods of using, arrays, preferably single molecule arrays according to invention, in the interrogation of the molecules in said array.

One of the advantages of the hydrogel-based molecular arrays and hydrogels of the invention, it has been found, is that omission of a covalent surface-modification step (particularly of the solid support) affords a surface having greater passivity than in the prior art, particularly when compared to those instances where the use of the silane-modifying agents described above with silica-based substrates are employed.

The provision of a surface which leads to as little as possible aspecific surface contamination is clearly advantageous where the hydrogels are used to construct arrays, such as microarrays, and preferably clustered arrays or SMAs, to be used in sequencing reactions.

Notwithstanding this, however, the hydrogels of this invention have functionality used in forming, or reacting with, the molecules which are arrayed. Consequentially, these hydrogels suffer too, albeit to a more limited extent than prior art hydrogels supported upon a functionally modified support, from a degree of aspecific nucleotide binding during sequencing.

Surprisingly, we have found that the solid-supported hydrogel-based molecular arrays of the invention may be still further improved by effecting certain modifications to these arrays after their formation but before initiation of any manipulation of, e.g. interrogation of, the molecules in the array. These arrays are of even greater advantageousness in, for example, polynucleotide sequencing reactions because the surfaces of the arrays may be rendered more passive, and thus less reactive, towards molecules such as optionally labelled nucleotides.

Accordingly the method according to the third aspect of the invention preferably contains the additional step of applying to the array so produced polyelectrolyte or neutral polymers. This improvement is of corresponding benefit to the other aspects of the invention directed to the arrays themselves, and the uses, and methods of using, such arrays.

The improvement to the solid-supported hydrogel-based molecular arrays, and uses of the arrays, of the invention is of general utility in the preparation and use of molecular arrays. It will be appreciated from the foregoing discussion that, in the preparation of arrays of molecules to date, particularly in the preparation of arrays of polynucleotides, these have invariably been assembled by initial preparation of the support, whether this be achieved by modification of a silica-based substrate, or formation of a PEM on a glass substrate, or formation of a hydrogel on glass or other solid supports. Only once the constitution of the solid support has been finalised is the array formed by reaction between the support and the molecules of interest. The array is then used, without further modification, in methods of analysis such as sequencing experiments whereby the molecules, typically polynucleotides, are interrogated.

Viewed from a still further aspect, therefore, the invention provides a method of modifying a molecular array, which molecular array comprises a plurality of molecules of interest, preferably biomolecules, immobilised to a surface of a support, said method comprising the step of applying to the array polyelectrolyte or neutral polymers.

Viewed from a still further aspect, the invention provides a molecular array obtainable according to the immediately preceding aspect of the invention.

Viewed from a still further aspect, the invention provides the use of a molecular array according to the immediately preceding aspect of the invention in any method of analysis which requires interrogation of the immobilized biomolecules, or of molecules bound thereto.

The present invention will now be further described. In the following passages different aspects of the invention are defined in more detail. Each aspect so defined may be combined with any other aspect or aspects unless clearly indicated to the contrary. In particular any feature indicated as being preferred or advantageous may be combined with any other feature or features indicated as being preferred or advantageous.

BRIEF DESCRIPTION OF THE DRAWINGS

In FIG. 8(a) the identity of the immobilised primer is indicated along the top of the plate. Templates were added in groups of four wells, as shown in the key. Hybridisation was carried out in two different buffers—a PCR buffer (PCR) and 5×SSC (SSC). Each immobilised primer was tested for hybridisation with a complementary primer (i.e. P5' is complementary to P5) and with a control non-complementary primer. FIG. 8(b) illustrates typical results in graphical form.

FIG. 12(a) shows experimental set-up and results. FIG. 12(b) provides a graphical representation of the results of typical hybridisation experiments for varying spacers versus P5' target.

DETAILED DESCRIPTION OF THE PREFERRED EMBODIMENT

Figure 1:
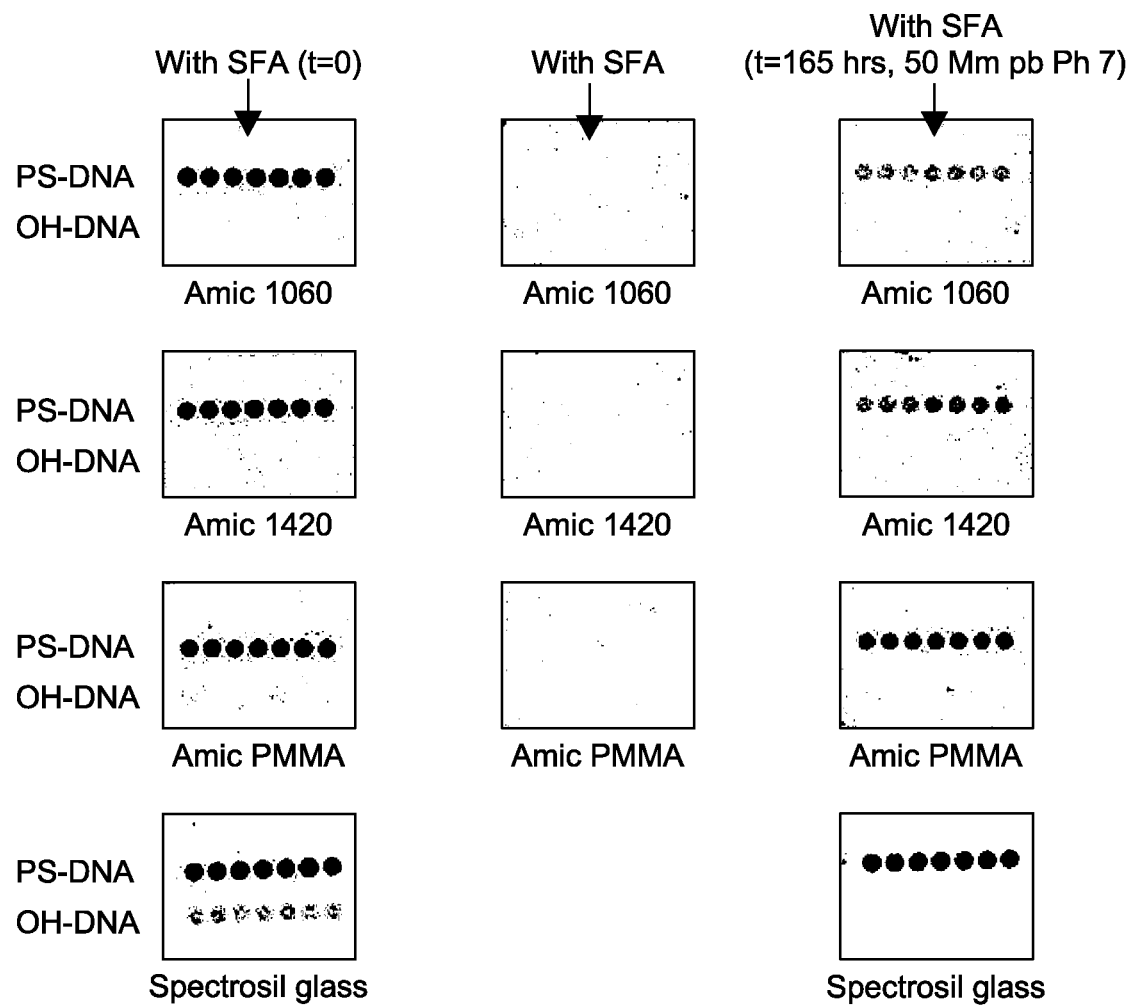
FIG. 1 shows images which show the detection of fluorescence from oligonucleotides immobilised on substrates both according to and not according to the invention, in accordance with Example 11. The improved binding of phosphorothioate-terminated DNA (PS-DNA) over hydroxyl-terminated DNA may be seen.

The invention, as described and claimed herein, provides an improved method for displaying molecules of interest, and particularly biomolecules (biological molecules) such as polynucleotides and proteins (preferably polynucleotides) displayed on the surface of a solid support, preferably a solid-supported hydrogel.

The solid upon which the hydrogel is supported is not limited to a particular matrix or substrate. Indeed, this is one of the advantages of the invention: the same chemistry used to modify silica-based substrates can be applied to other solid supports and allows the solid support to be adapted to suit any particular application to which it is desired to be put rather than being constrained by the surface chemistry it is possible to perform on any given support. Solids which may be of use in the practise of this invention thus include silica-based substrates, such as glass, fused silica and other silica-containing materials; they may also be silicone hydrides or plastic materials such as polyethylene, polystyrene, poly(vinyl chloride), polypropylene, nylons, polyesters, polycarbonates and poly (methyl methacrylate). Preferred plastics material are poly (methyl methacrylate), polystyrene and cyclic olefin polymer substrates. Alternatively, other solid supports may be used such as gold, titanium dioxide, or silicon supports. The foregoing lists are intended to be illustrative of, but not limited to, the invention. Preferably, the support is a silica-based material or plastics material such as discussed herein.

Advantages in using plastics-based substrates in the preparation and use of molecular arrays include cost: the preparation of appropriate plastics-based substrates by, for example injection-moulding, is generally cheaper than the preparation, e.g. by etching and bonding, of silica-based substrates. Another advantage is the nearly limitless variety of plastics allowing fine-tuning of the optical properties of the support to suit the application for which it is intended or to which it may be put.

Where metals are used as substrates, this may be because of the desired application: the conductivity of metals can allow modulation of the electric field in DNA-based sensors. In this way, DNA mismatch discrimination may be enhanced, the orientation of immobilised oligonucleotide molecules can be affected, or DNA kinetics can be accelerated.

Preferably the support is silica-based but the shape of the support employed may be varied in accordance with the application for which the invention is practiced. Generally, however, slides of support material, such as silica, e.g. fused silica, are of particular utility in the preparation and subsequent interrogation of molecules. Of particular use in the practice of the invention are fused silica slides sold under the trade name SPECTRASIL™. This notwithstanding, it will be evident to the skilled person that the invention is equally applicable to other presentations of solid support (including silica-based supports), such as beads, rods and the like.

The genesis of the invention is the recognition by the inventors that the surface of the support need not be covalently modified in order for a hydrogel to be immobilised thereto. As described herein, the step of covalent surface modification may be omitted when the comonomer mixture described and claimed herein is used to produce a hydrogel.

If it is desired to display molecules of interest, e.g. biomolecules, these may be any biological molecule which it is desired to analyse. Of particular interest are polypeptides or proteins (including enzymes) and polynucleotides, with polynucleotides being particularly preferred.

As used herein, the term "polynucleotide" refers to nucleic acids in general, including DNA (e.g. genomic DNA cDNA), RNA (e.g. mRNA), synthetic oligonucleotides and synthetic nucleic acid analogs. Polynucleotides may include natural or non-natural bases, or combinations thereof and natural or non-natural backbone linkages, e.g. phosphorothioates, PNA or 2'-O-methyl-RNA, or combinations thereof.

Whilst it will be appreciated that the solid-supported hydrogels of the invention are useful for the presentation of many different types of molecules, the hydrogels are of particular use in the formation of arrays of polynucleotides and their subsequent analysis. For this reason, the majority of the subsequent discussion will focus upon the utility of the supported hydrogels of the invention in the preparation of polynucleotide arrays (both single molecule arrays and microarrays, such as clustered arrays formed by nucleic acid amplification) although it is to be understood that such applications in no way limit the invention. Moreover, since silica-based supports are typically used to support hydrogels and hydrogel arrays, the subsequent discussion will focus on the use of silica-based supports. Again, this is not to be considered as a limitation of the invention; rather this is demonstrative of a particular advantage of the invention for improving procedures directed to constructing arrays of molecules on silica-supported hydrogels. The improvement offered will be evident from a review of the prior art.

WO00/31148 discloses polyacrylamide hydrogels and polyacrylamide hydrogel-based arrays in which a so-called polyacrylamide prepolymer is formed, preferably from acrylamide and an acrylic acid or an acrylic acid derivative containing a vinyl group. Crosslinking of the prepolymer may then be effected. The hydrogels so produced are solid-supported, preferably on glass. Functionalisation of the solid-supported hydrogel may also be effected.

WO01/01143 describes technology similar to WO00/31148 but differing in that the hydrogel bears functionality capable of participating in a [2+2] photocycloaddition reaction with a biomolecule so as to form immobilised arrays of such biomolecules. Dimethylmaleimide (DMI) is a particularly preferred functionality. The use of [2+2] photocycloaddition reactions, in the context of polyacrylamide-based microarray technology is also described in WO02/12566 and WO03/014392.

U.S. Pat. No. 6,465,178 discloses the use of reagent compositions in providing activated slides for use in preparing microarrays of nucleic acids; the reagent compositions include acrylamide copolymers. The activated slides are stated to be particularly well suited to replace conventional (e.g. silylated) glass slides in the preparation of microarrays.

WO00/53812 discloses the preparation of polyacrylamide-based hydrogel arrays of DNA and the use of these arrays in replica amplification.

None of the prior art described herein discloses the preparation of a solid-supported hydrogel wherein the solid support is not covalently modified.

Once hydrogels have been formed, molecules may then be attached to them so as to produce molecular-arrays, if desired. Attachment has been effected in different ways in the prior art. For example, U.S. Pat. No. 6,372,813 teaches immobilisation of polynucleotides bearing dimethylmaleimide groups to the hydrogels produced which bear dimethylmaleimide groups by conducting a [2+2] photocycloaddition step between two dimethylmaleimide groups—one attached to the polynucleotide to be immobilised and one pendant from the hydrogel.

Where the molecular array is formed after generation of the hydrogel, two strategies have been employed to achieve this end. Firstly, the hydrogel may be modified chemically after it is produced. Problems with this approach include an overall low efficiency in the preparation of the array and the low stability relating to the attachment chemistry, particularly upon exposure to high temperatures, ionic solutions and multiple wash steps.

A more common alternative is to effect polymerisation with a comonomer having a functionality primed or pre-activated to react with the molecules to be arrayed.

Alternatives to initial formation of hydrogels followed by subsequent arraying of molecules thereto have been described in the prior art where the array is formed at the same time as the hydrogel is produced. This may be effected by, for example, direct copolymerisation of acrylamide-derivatized polynucleotides. An example of this approach is described in WO01/62982 in which acrylamide-derivatized polynucleotides are mixed with solutions of acrylamide and polymerisation is effected directly.

Mosaic Technologies (Boston, Mass., USA) produce ACRYDITE™ (an acrylamide phosphoramidite) which can be reacted with polynucleotides prior to copolymerisation of the resultant monomer with acrylamide.

Efimov et al. (*Nucleic Acids Research*, 1999, 27 (22), 4416-4426) disclose a further example of a simultaneous formation of hydrogel/array in which copolymerisation of acrylamide, reactive acrylic acid derivatives and the modified polynucleotides having 5'- or 3'-terminal acrylamide groups is effected.

The above-described techniques, however, in which the hydrogel is generated simultaneously with the array by introduction of appropriate comonomers bearing the molecules of interest, suffer from problems including damage to the molecules of interest during polymerisation.

A variety of solid supports have been used in the prior art to generate hydrogel-based solid-supported molecular arrays. These include those supports discussed earlier. Generally the preferred solid support comprises a silica-based substrate. Examples of silica-based substrates include fused silica and glass.

To the best of our knowledge, in all instances of silica-based supported hydrogels described in the prior art the silica is chemically modified in some way so as to attach covalently a chemically reactive group capable of reacting with either the hydrogel or a partially formed hydrogel (e.g. a prepolymer (PRP)). The surface-activating agent is typically an organosilicon (organosilane) compound. Most commonly, it is γ-methacryloxypropyltrimethoxysilane, known as "Bind Silane" or "Crosslink Silane" and commercially available from Pharmacia, although other silicon-based surface-activating agents are also known, such as monoethoxydimethylsilylbutanal, 3-mercaptopropyl-trimethoxysilane and 3-aminopropyltrimethoxysilane (all available from Aldrich). In this way, pendant functional groups such as amine groups, sulfhydryl groups, aldehydo groups or polymerisable groups (e.g. olefins) may be attached to the silica.

It will be clear from the preceding discussion that the invention is particularly useful when the solid support used is silica-based since the silica-based support need not be covalently modified by its preactivation with a silylating agent as described above in order to immobilise the hydrogel thereto. Clearly, however, the polymers described herein may still be (in certain aspects of the invention) attached to silica-based supports which have been surface-activated, e.g. with an organosilane molecule as described above; the full advantages of the invention will, however, not be obtained in this way. They may also be, of course, attached to the other solid supports disclosed herein, in particular plastics such as poly(methyl methacrylate) and polyolefins. Such plastics are readily available commercially, e.g. from Arnie, Corning, Zeon Chemical Ltd and others.

The surface-modification of silica-based solid supports by means other than covalent attachment of an organosilicon moiety is not excluded from the scope of this invention. Preferably, however, no activation of the silica—by covalent modification of a surface thereof or by any other means—is effected prior to effecting polymerisation thereon.

It will be understood that the terms such as "covalent surface-modification", "covalent surface-modifying" and "covalent surface-modified" do not embrace the simple cleaning and/or drying of substrates, particularly silica substrates, prior to their use. Generally such steps will be conducted prior to any polymerisation but do not constitute a surface-modifying step since no covalent modification of a surface is essentially effected by such steps.

Where the substrate is silica-based, cleaning will be achieved by contact with one or more organic solvents such as acetone, isopropanol (IPA), ethanol and the like, or with water or aqueous acidic or alkaline solutions such as dilute hydrochloric or sulphuric acids or dilute sodium hydroxide. Silica-based supports may be also cleaned by contact with a detergent solution (e.g. Decon 90). These various cleaning steps may be conducted individually or in combination, e.g. sequentially. Drying may be effected, for example, by heating of silica slides at temperatures of from 40° C. to 200° C., preferably 80° C. to 150° C. for between 5 minutes to 24 hours, preferably at temperatures of around 120° C., and preferably for 1 to 2 hours.

The cleaning and drying steps described above will be and are understood by those skilled in the art not to constitute any form of covalent surface modification (and in particular no form of covalent surface modification in which an organosilicon (organosilane) moiety is attached). Such steps serve to effect removal of surface contamination (e.g. dirt or dust) and will generally be conducted prior to use of silica-based materials in most scientific applications. Heating of glass to very high temperatures (e.g. 1000° C. or higher or even 300° C. or higher) or by contact with materials known to dissolve, or etch glass (such as hydrofluoric acid), whilst unlikely to be conducted in the cleaning of silica-based substrates in advance of practice of this invention, is not to be considered as constituting a form of surface modification.

For substrates that are not silica-based other cleaning techniques may be appropriate, as will be apparent to those skilled in the art. For example, plastic substrates may be cleaned by contact with (e.g. immersion in) any convenient detergent (Decon 90 is an example) followed by thorough rinsing with water, preferably purified water such as MilliQ, prior to drying.

The methods by which the mixture of comonomers are polymerised in the invention are not characteristic of this invention and will be known to the skilled person (e.g. by recourse to Sambrook et al. (supra). Generally, however, the polymerisation will be conducted in an aqueous medium, and polymerisation initiated by any suitable initiator. Potassium or ammonium persulfate as an initiator is typically employed. Tetramethylethylenediamine (TMEDA or TEMED) may be and generally is used to accelerate the polymerisation.

It is important to note that, in contrast to the teaching of hydrogel preparation in the prior art concerned with the preparation of molecular arrays, it is not necessary that a polyunsaturated crosslinking agent such as bisacrylamide or pentaerythritol tetraacrylate is present in the mixture which is polymerised; nor is it necessary to form PRP-type intermediates and crosslink them. It is one of the surprising features of the invention that satisfactory stability of the immobilised array may be achieved in the absence of such crosslinking agents or PRP crosslinking steps. The absence of a polyunsaturated crosslinking agent (such as bisacrylamide or pentaerythritol tetraacrylate) is a preferred feature in all aspects of this invention directed toward hydrogels, or uses or methods of the preparation thereof. Thus it is a preferred feature of such aspects of the invention that the mixture to be polymerised does not comprise such a polyunsaturated crosslinking agent and that the monomers to be polymerised consist essentially of those defined in claim 1 (i.e. no polyunsaturated crosslinking monomer is included in the mixture).

Generally, in producing hydrogels according to this invention, only one compound of formulae (I) or (II) will be used.

We have found that use of a compound of the formulae (I) or (II) permits formation of a hydrogel capable of being immobilised to solid supports, preferably silica-based solid supports. The compounds of these formulae comprise portions A, B and C as defined herein.

Biradical A may be oxygen or N(R) wherein R is hydrogen or a $C_{1-5}$ alkyl group. Preferably, R is hydrogen or methyl, particularly hydrogen. Where R is a $C_{1-5}$ alkyl group, this may contain one or more, e.g. one to three substituents. Preferably, however, the alkyl group is unsubstituted.

Biradical B is a predominantly hydrophobic linking moiety, connecting A to C and may be an alkylene biradical of formula —$(CH_2)_n$—, wherein n is from 1 to 50. Preferably n is 2 or more, e.g. 3 or more. Preferably n is 2 to 25, particularly 2 to 15, more particularly 4 to 12, for example 5 to 10.

Where n in —$(CH_2)_n$— is 2 or more, one or more biradicals —$CH_2CH_2$(-ethylene-) may be replaced with ethenylene or ethynylene biradicals. Preferably, however, the biradical B does not contain such unsaturation.

Additionally, or alternatively, where n in —$(CH_2)_n$— is 1 or more, one or more methylene radicals —$CH_2$— in B may be replaced with a mono- or polycyclic biradical which preferably comprises 5 to 10 carbon atoms e.g. 5 or 6 carbon atoms. Such cyclic biradicals may be, for example, 1,4-, 1,3- or 1,2-cyclohexyl biradicals. Bicyclic radicals such as naphthyl or decahydronaphthyl may also be employed. Corresponding heteroatom-substituted cyclic biradicals to those homocyclic biradicals may also be employed, for example pyridyl, piperidinyl, quinolinyl and decahydroquinolinyl.

It will be appreciated that the scope of —B— is thus not particularly restricted. Most preferably, however, —B— is a simple, unsubstituted, unsaturated alkylene biradical such as a $C_3$-$C_{10}$ alkylene group, optimally $C_5$-$C_8$, such as n-pentylene: —$(CH_2)_5$—.

Where an alkyl group (or alkylene, alkenylene etc) is indicated as being (optionally) substituted, substituents may be selected from the group comprising hydroxyl, halo (i.e. bromo, chloro, fluoro or iodo), carboxyl, aldehydo, amine and the like. The biradical —B— is preferably unsubstituted or substituted by fewer than 10, preferably fewer than 5, e.g. by 1, 2 or 3 such substituents.

Group C serves to permit attachment of molecules of interest after formation of the hydrogel. The nature of Group C is thus essentially unlimited provided that it contains a functionality allowing reaction between the hydrogel and molecules of interest. Preferably, such a functionality will not require modification prior to reaction with the molecule of interest and thus the C group is ready for direct reaction upon formation of the hydrogel.

Preferably such a functionality is a hydroxyl, thiol, amine, acid (e.g. carboxylic acid), ester and haloacetamido, haloacetamido and in particular bromoacetamido being particularly preferred. Other appropriate C groups will be evident to those skilled in the art and include groups comprising a single carbon-carbon double bond which is either terminal (i.e. where a C group has an extremity terminating in a carbon-carbon double bond) or where the carbon-carbon double bond is not at a terminal extremity. When a C group comprises a carbon-carbon double bond, this is preferably fully substituted with $C_{1-5}$ alkyl groups, preferably methyl or ethyl groups, so that neither carbon atom of the C=C moiety bears a hydrogen atom.

The C moiety may thus comprise, for example, a dimethylmaleimide moiety as disclosed in U.S. Pat. No. 6,372,813, WO01/01143, WO02/12566 and WO03/014394.

The (meth)acrylamide or (meth)acrylate of formula (I) or (II) which is copolymerised with acrylamide, methacrylamide, hydroxyethyl methacrylate or N-vinyl pyrrolidinone is preferably an acrylamide or acrylate, i.e., of formula (I). More preferably it is an acrylamide and still more preferably it is an acrylamide in which A is NH.

The reaction between a comonomer of formula (I) or (II) and acrylamide, methacrylamide, hydroxyethyl methacrylate or N-vinyl pyrrolidinone methacrylamide, particularly acrylamide, has been found to afford hydrogels particularly suitable for use in the generation of molecular arrays. However, it will be appreciated by those skilled in the art that analogous copolymers may be formed by the reaction between comonomers of formula (I) or (II) and any vinylogous comonomer, hydroxyethylmethacrylate and n-vinyl pyrrolidinone being two examples of such vinylogous comonomers.

Control of the proportion of monomer of formula (I) or (II) to that of the first comonomer (e.g. acrylamide and/or methacrylamide, preferably acrylamide) allows adjustment of the physical properties of the hydrogel obtained on polymerisation. It is preferred that the comonomer of formula (I) or (II) is present in an amount of mol %, preferably mol % (relative to the total molar quantity of comonomers) in order for the hydrogel to have optimum thermal and chemical stability under conditions typically encountered during the preparation, and subsequent manipulation, of the molecular arrays produced from the hydrogels. Preferably, the amount of comonomer of formula (I) or (II) is less than or equal to about 5 mol %, more preferably less than or equal to about 4 mol %. Typical amounts of comonomer of formula (I) or (II) used are 1.5-3.5 mol %, exemplified herein by about 2% and about 3%.

The amounts of acrylamide or methacrylamide from which the hydrogels are primarily constructed are those typically used to form hydrogels, e.g. about 1 to about 10% w/v, preferably less than 5 or 6% w/v, e.g. about 1 to about 2% w/v. Again, of course, the precise nature of the hydrogel may be adjusted by, in part, control of the amount of acrylamide or methacrylamide used.

When forming the hydrogels, acrylamide or methacrylamide may be dissolved in water and mixed with a solution of a comonomer of formula (I) or (II). The latter may be conveniently dissolved in a water-miscible solvent, such as dimethylformamide (DMF), or water itself. The most appropriate solvent may be selected by the skilled person and shall depend upon the structure of the comonomer of formula (I) or (II).

The methods by which the monomers of formula (I) or (II) are synthesised will be evident to those skilled in the art. By way of example, the synthesis of a particularly preferred monomer (of formula (I) wherein A NH, —B═══(CH$_2$)$_5$— and —C══N(H)—C(═O)CH$_2$Br is provided as an example hereinafter.

As noted above, the general methods by which the polymerisation is carried out are known to those skilled in the art. For example, generally acrylamide or methacrylamide is dissolved in purified water (e.g. MilliQ) and potassium or ammonium persulfate dissolved separately in purified water. The comonomer of formula (I) or (II) may be conveniently dissolved in a water-miscible organic solvent, e.g. glycerol, ethanol, methanol, dimethylformamide (DMF) etc. TEMED may be added as appropriate. Once formulated (a typical preparation is described in the examples), the mixture is polymerised with as little delay as possible after its formulation.

The polymerisation process may be conducted by any convenient means. Several examples are described in the experimental section below.

The hydrogels according to this invention are of particular utility in the preparation of arrays of molecules, particularly single molecule arrays (SMAs) or clustered arrays and in particular SMAs or clustered arrays of polynucleotides.

It is noted above that it is a surprising feature of relevant aspects of this invention that it is possible to omit the inclusion of a polyunsaturated crosslinking agent. Where such a crosslinking agent is omitted, as is preferable, it is possible to make thinner hydrogels than have been achievable heretofore. In particular, omission of such crosslinking agents allows preparation of hydrogels having thicknesses of less than about 100 nm, for example less than 75 nm; the hydrogels may be less than about 50 nm thick.

Such hydrogels are of particular use where they are used to generate arrays, in particular single molecule arrays or clustered arrays, particularly of nucleotides, and in the interrogation of such arrays wherein fluorescently labelled nucleotides are incorporated into a nascent polynucleotide and then detected. Such techniques are described in greater detail hereinafter.

There are a number of advantages of the hydrogels produced according to this invention. With particular regard to silica-based substrates, the invention allows the avoidance of the covalent chemical modification (especially with silicon-containing agents) of the silica-based substrate in order for the hydrogels produced on the support be immobilised thereto. Thus, the invention permits immobilisation of hydrogels on a variety of solid supports upon which such immobilisation has not been reported previously.

By "immobilising" of a hydrogel on a support is meant that the supported hydrogels are associated with the support in such a way so as to remain as a layer upon the support under conditions encountered during preparing and manipulating (e.g. interrogating) molecular arrays. Such preparations and manipulations are described in greater detail hereinafter and are known to those skilled in the art.

A further advantage of the supported hydrogels of the invention is avoidance of the need for chemical modification of the hydrogel (i.e. post polymerisation) in order to attach of molecules of interest. With the "e" groups described herein, appropriately functionalised molecules may be attached directly to the hydrogel.

A further advantage is the passivity, i.e. the essential lack of reactivity, of the surface of the hydrogel towards non-specific adherence of molecules (e.g. fluorescently labelled nucleotides) to the surface; such adherents would otherwise create unwanted "noise" during subsequent manipulation of molecular arrays formed from the hydrogels, particularly in the manipulation of SMAs or clustered arrays.

As noted above, it has been found that omission of a covalent surface-modification step results in a surface having greater passivity than in the prior art, particularly when compared to those instances where the use of the silane-modifying agents described above with silica-based substrates are employed.

The provision of a surface which leads to as little as possible aspecific surface contamination is clearly advantageous where the hydrogels are used to construct arrays to be used in SMA applications. Of course, where the hydrogels are used to construct clustered microarrays, minimising surface contamination to the greatest extent possible is also advantageous.

In accordance with preferred aspects of the invention, the solid-supported hydrogel-based molecular arrays of the invention may be treated with polyelectrolyte or neutral polymers to afford arrays, preferably SMAs or clustered arrays, particularly SMAs or clustered arrays of polynucleotides, the surfaces of which have enhanced passivity towards, for example, aspecific binding with nucleotides (e.g. labelled nucleotides) used in sequencing and other interrogative methods of using the arrays. Also, the invention, as described and claimed herein, provides an improved method by which molecules of interest (preferably biomolecules such as those identified above), preferably polynucleotides and proteins (especially preferably polynucleotides) may be displayed by modifying existing, i.e. preprepared, arrays of molecules. It will be appreciated that, since this aspect of the invention lies in the modification of existing molecular arrays, the nature of the molecular array treated according to the method of the invention is not of any particular importance. This notwithstanding, it is preferred that the arrays treated are in accordance with the fourth aspect of this invention. Likewise, the nature of the biomolecules arrayed, or the means by which they are arrayed, is of lesser importance than the requirement for the modification step whereby the array is treated with polyelectrolyte or neutral polymers.

On account of the particular utility of molecular arrays, preferably SMAs or clustered arrays, most preferably SMAs or clustered arrays of polynucleotides, in sequence determination methods, the preceding discussion has focused, and subsequent discussion shall focus, on this utility of the invention although it is to be understood that the invention is not to be considered to be so limited.

Similarly, the make-up of the solid support of the array to be modified, or the type of the array to be modified is not of as great importance as the manner in which it is treated (modified) according to the invention. SMAs and clustered arrays, however, and preferably SMAs and clustered arrays of polynucleotides are particularly advantageous.

The term "single molecule array" or "SMA" as used herein refers to a population of polynucleotide molecules, distributed (or arrayed) over a solid support, wherein the spacing of any individual polynucleotide from all others of the population is such that it is possible to effect individual resolution, or interrogation, of the polynucleotides. The target nucleic acid molecules immobilised onto the surface of the solid support should thus be capable of being resolved by optical means. This means that, within the resolvable area of the particular imaging device used, there must be one or more distinct signals, each representing one polynucleotide. This may be achieved, preferably wherein the spacing between adjacent polynucleotide molecules on the array is at least 100 nm, more preferably at least 250 nm, still more preferably at least 300 nm, even more preferably at least 350 nm. Thus, each molecule is individually resolvable and detectable as a single molecule fluorescent point, and fluorescence from said single molecule fluorescent point also exhibits single step photobleaching.

Clusters of substantially identical molecules do not exhibit single point photobleaching under standard operating conditions used to detect/analyze molecules on arrays. The intensity of a single molecule fluorescence spot is constant for an anticipated period of time after which it disappears in a single step. In contrast, the intensity of a 'fluorescence spot comprised of two or more molecules, for example, disappears in two or more distinct and observable steps, as appropriate. The intensity of a fluorescence spot arising from a cluster consisting of thousands' of similar molecules, such as those present on the arrays consisting of thousands of similar molecules at any given point, for example, would disappear in a pattern consistent with an exponential decay. The exponential decay pattern reflects the progressive loss of fluorescence by molecules present in the cluster and reveals that, over time, fewer and fewer molecules in the spot retain their fluorescence.

The term "clustered array" refers to an array wherein distinct regions or sites on the array comprise multiple polynucleotide molecules that are not individually resolvable by optical means. Depending on how the array is formed each region or site on the array may comprise multiple copies of one individual polynucleotide molecule or even multiple copies of a small number of different polynucleotide molecules (e.g. multiple copies of two complementary nucleic acid strands). In a preferred embodiment the term "clustered array" refers to an array produced by solid-phase amplification of a target or template polynucleotide, wherein amplified copies of the target or template become covalently bound to the solid support during amplification.

Clustered arrays of nucleic acid molecules may be produced using techniques generally known in the art. By way of example, WO 98/44151 and WO 00/18957 both describe methods of nucleic acid amplification which allow amplification products to be immobilised on a solid support in order to form arrays comprised of clusters or "colonies" of immobilised nucleic acid molecules. A further method for the preparation of clustered arrays on a solid-support bound hydrogel is described in further detail below and in the accompanying examples. It will be appreciated that the arrays of the invention, in all aspects, may be arrays of clusters of molecules. Such arrays are a preferred embodiment of all aspects of the invention.

The support for the molecular array (hydrogel-based or otherwise) which may be modified according to the invention is not limited to a particular matrix or substrate. Supports which may be of use in the practise of this invention are as described above.

Some supports to which biomolecules, such as polynucleotides, are attached are silica-based supports themselves. In certain embodiments of the invention these may be covalently modified in some way so as to allow covalent attachment of either polynucleotides, or to immobilise a chemically reactive group hydrogel or a partially formed hydrogel (e.g. a prepolymer). The surface-activating agent is typically an organosilicon (organosilane) compound such as those listed above.

Arrays in which polynucleotides have been directly attached to silica-based supports are those for example disclosed in WO 97/04131, wherein hairpin polynucleotides are immobilised on a glass support by reaction between a pendant epoxide group on the glass with an internal amino group held within the loop.

Zhao et al. (Nucleic Acids Research, 2001, 29(4), 955959} disclose the formation of a hairpin polynucleotide which contains multiple phosphorothioate moieties in the loop. The moieties are used to anchor, in more than one position, the hairpin DNA to glass slides pre-activated with bromoacetamidopropylsilane.

The work of Zhao developed upon earlier work of Pirrung et al. (*Langmuir,* 2000, 16, 2185-2191) in which the authors report that 5'-thiophosphate-terminating oligonucleotides could be attached to glass, pre-activated with mono- and dialkoxylated silanes and bromoacetamide.

In addition, we disclose in our copending International patent application number PCT/GB2004/004707 arrays of hairpin polynucleotides attached to a solid support, e.g. for use in the preparation of SMAs, by reaction of a sulfur-based nucleophile with the solid support. The sulfur-based nucleophile may be directly attached to the hairpin although it is preferably indirectly attached through a linker. Attachment is by way of an internal nucleotide within the hairpin, that is to say that the sulfur-based nucleophile is not connected directly or through a linker to a nucleotide at either terminus of the hairpin.

Still further example of arrays are those in which biomolecules, preferably polynucleotides, are attached to hydrogels supported upon silica-based or other solid supports. Silica-based supports are typically used to support hydrogels and hydrogel arrays as described in WO00/31148, WO01/01143, WO02/12566, WO03/014392, U.S. Pat. No. 6,465,178 and WO00/53812.

The solid supports for such hydrogels are preferably silica-based since the silica-based support need not be covalently modified by preactivation with a silylating agent as described above in order to immobilise the hydrogel thereto. Clearly, however, such hydrogels may still be attached to silica-based supports which have been surface-activated, e.g. with an organosilane molecule as described above.

A further type of molecular array which may be treated according to this invention are PEM-supported molecular arrays of the type described by Braslaysky et al. (infra) I and Kartlov et al. (infra).

There are thus three main types of molecular array which may be treated according to this invention:
  (1) arrays directly supported onto silica-based supports;
  (2) hydrogel-based molecular arrays; and
  (3) PEM-supported molecular arrays.

Of these the hydrogel-based molecular arrays are most preferred, and in particular hydrogel-based arrays according to the fourth aspect of the invention primarily because of the simplicity with which these may be constructed. Whilst, such hydrogels are advantageous on account of the passivity of the surface, we have found that the surface treatment of this invention leads to still greater passivity, and thus utility in sequencing reactions and the like, of the resultant molecular arrays.

According to this invention, the surface of an existing array of biomolecules, preferably of polynucleotides, is modified by treatment with a mixture comprising polyelectrolyte a mixture comprising neutral polymers, or a mixture comprising both polyelectrolytes and neutral polymers.

Polyelectrolytes are large, generally polymeric, molecules containing a plurality of ionisable groups. Examples include polyallylamine (PAL), commercially available as polyallylamine hydrochloride (PAL.HCl), polyacrylic acid (PAA), poly(styrene sulfonate) (PSS) and polyethyleneimine (PEI). The degree to which they are ionised is dependent upon the pH of the medium in which they are present.

In the context of DNA sequencing, we have found that a combination of more than one polyelectrolyte is particularly advantageous when modifying molecular arrays. As an example, we have found that the sequential application of PAL.HCl followed by PAA to be particularly preferred.

The conditions under which the arrays may be treated include exposing them to solutions, or suspensions of polyelectrolyte or neutral polymer. Preferably these solutions or suspensions are aqueous. Particularly preferably the pH of the solution or suspension is higher than 6 and less than 8.5, more preferably from 6.5 to 8, still more preferably from 6.5 to 7.5, more preferably approximately neutral, or about pH 7.

As an alternative to polyelectrolytes, neutral polymers, e.g. polyethylene glycols, such as those commercially available, e.g. PEG 8000 available from Sigma, may be used.

Of course both polyelectrolyte and neutral polymers may be used.

It will be appreciated that the treatment of molecular arrays according to this invention shall generally, particularly in the case of planar arrays, serve to deposit layers of polyelectrolyte and/or polymers.

When polynucleotides are arrayed in molecular arrays according to the various aspects of this invention, including the solid-supported hydrogel-based molecular arrays of the invention, these are preferably hairpin polynucleotides comprising a polynucleotide duplex which may be used to retain a primer and a target polynucleotide in spatial relationship. Preferably the target polynucleotide is present at the 5' end and the primer is present at the 3' end although hairpin polynucleotides where the primer is present at the 5' end and the target polynucleotide is present at the 3' end are also embraced by this invention.

As used herein, the term "interrogate" can refer to any interaction of a molecule on the array with any other chemical or molecule and may also refer to any analysis of a detectable signal from a molecule on the array or any other molecule which is bound thereto or associated therewith. In one embodiment "interrogation" encompasses a target polynucleotide on the array functioning as a template upon which DNA polymerase acts. In other words, "interrogating" can encompass contacting the target polynucleotides with another molecule, e.g., a polymerase, a nucleoside triphosphate, a complementary nucleic acid sequence, wherein the physical interaction provides information regarding a characteristic of the arrayed target polynucleotide. The contacting can involve covalent or non-covalent interactions with the other molecule. As used herein, "information regarding a characteristic" means information about the identity or sequence of one or more nucleotides in the target polynucleotide, the length of the polynucleotide, the base composition of the polynucleotide, the Tm of the polynucleotide, the presence of a specific binding site for a polypeptide, a complementary nucleic acid or other molecule, the presence of an adduct or modified nucleotide, or the three-dimensional structure of the polynucleotide.

The spatial relationship between primer and target polynucleotide present in hairpin polynucleotides permits improved sequence analysis procedures to be conducted. Maintenance of the spatial relationship is made possible not only by the hydrogen bonds formed on hybridisation, but also by the tethering of a known primer to the target polynucleotide. The fixing of the primer, as part of the hairpin structure, to the hydrogel support, ensures that the primer is able to perform its priming function during a polymerase-based sequencing procedure, and is not removed during any washing step in the procedure.

There are many different ways of forming a hairpin structure so as to incorporate the target polynucleotide. A preferred method is to form a first molecule (which may contain a non-backbone sulfur-based nucleophile attached through a linker) capable of forming a hairpin structure, and ligate the target polynucleotide to this. It is possible to ligate any desired target polynucleotide to the hairpin construct before or after arraying the hairpins on the solid support. Alternatively, a first polynucleotide may be ligated before arraying and a second ligated after arraying. It is, of course, also possible to introduce a nucleophile (preferably a sulfur-based nucleophile) after such a ligation.

Where a target polynucleotide is a double-stranded DNA, this may be attached to the stem of the hairpin by ligating one strand to the hairpin polynucleotide and removing the other strand after the ligation.

The target polynucleotide may be genomic DNA purified using conventional methods. The genomic DNA may be PCR-amplified or used directly to generate fragments of DNA using either restriction endonucleases, other suitable enzymes, a mechanical form of fragmentation or a non-enzymatic chemical fragmentation method. In the case of fragments generated by restriction endonucleases, hairpin structures bearing a complementary restriction site at the end of the first hairpin may be used, and selective ligation of one strand of the DNA sample fragments may be achieved by one of two methods.

Method 1 uses a hairpin containing a phosphorylated 5' end. Using this method, it may be necessary to first de-phosphorylate the restriction-cleaved genomic or other DNA fragments prior to ligation such that only one sample strand is covalently ligated to the hairpin.

Method 2: in the design of the hairpin, a single (or more) base gap can be incorporated at the 3' end (the receded strand) such that upon ligation of the DNA fragments only one strand is covalently joined to the hairpin. The base gap can be formed by hybridising a further separate polynucleotide to the 5-end of the first hairpin structure. On ligation, the DNA fragment has one strand joined to the 5-end of the first hairpin, and the other strand joined to the 3-end of the further polynucleotide. The further polynucleotide (and the other stand of the fragment) may then be removed by disrupting hybridisation.

In either case, the net result should be covalent ligation of only one strand of a DNA fragment of genomic or other DNA to the hairpin. Such ligation reactions may be carried out in solution at optimised concentrations based on conventional ligation chemistry, for example, carried out by DNA ligases or non-enzymatic chemical ligation. Should the fragmented DNA be generated by random shearing of genomic DNA or polymerase, then the ends can be filled in with Klenow fragment to generate blunt-ended fragments which may be blunt-end-ligated onto blunt-ended hairpins. Alternatively, the blunt-ended DNA fragments may be ligated to polynucleotide adapters which are designed to allow compatible ligation with the sticky-end hairpins, in the manner described hereinbefore.

Polynucleotides, particularly hairpin polynucleotides, may be bound directly to the "C" groups of hydrogels, if present, by, for example, immobilising them through a covalent bond between each polynucleotide (by way of a nucleophile, preferably sulfur-based nucleophile) and the "C" group. In doing so it is thus possible to generate arrays, e.g. microarrays or SMAs, preferably SMAs, of the hairpin polynucleotides.

The precise density of the arrays is not critical. For single molecule resolution, in fact, the higher the density of hairpin polynucleotide molecules arrayed the better since more information may be obtained from anyone experiment. For example, there may be at least $10^3$ molecules/cm$^2$, preferably at least $10^5$ molecules/cm$^2$ and most preferably $10^6$-$10^9$ molecules/cm$^2$. Particularly preferably, the density of sample molecules is at least $10^7$/cm$^2$, typically it is approximately $10^8$-$10.^9$/cm$^2$.

Such "high density" arrays are in contrast to those arrays such as those so described in the prior art which are not necessarily as high or, e.g. in the many molecule arrays of—Fodor et al (supra), which comprise clusters of polynucleotides comprising a plurality of tightly packed polynucleotides that are resolvable at the level of the cluster, not at the level of the polynucleotides, are too high to allow single molecule resolution. By arraying the polynucleotides at a density that they can be considered to be single molecules, i.e. each can be individually resolved, a SMA is created.

The terms "individually resolved" and "individual resolution" are used herein to specify that, when visualised, it is possible to distinguish one molecule on the array from its neighbouring molecules. Separation between individual molecules on the array will be determined, in part, by the particular technique used to resolve the individual molecules. It will usually be the target polynucleotide portion that is individually resolved, as it is this component which is intended to be interrogated, e.g. by the incorporation of detectable bases.

Covalent bonding, where present, between the "C" groups in the hydrogel and polynucleotides (e.g. hairpin polynucleotides or oligonucleotide primers used for formation of clustered arrays by solid-phase amplification), may be effected by any convenient means.

Preferably, where the "C" group is a haloacetamido group, polynucleotides bearing sulfur-containing nucleophilic groups are used. Examples of appropriate sulfur nucleophile-containing polynucleotides are disclosed in Zhao et al (*Nucleic Acids Research*, 2001, 29(4), 955-959) and Pirrung et al (*Langmuir*, 2000, 16, 2185-2191).

However, the preferred class of sulfur-based nucleophiles pendant from the polynucleotides for reaction with the reactive groups on the hydrogels are not particularly restricted. The sulfur-based nucleophile may thus be a simple thiol (—SH wherein — denotes the bond or linker connecting the thiol to the remainder of the polynucleotide). Further examples of sulfur-based nucleophiles include a moiety of the formula (III):

(III)

(wherein — denotes the bond or linker connecting the sulfur-based nucleophile to the remainder of the polynucleotide; X represents an oxygen atom, a sulfur atom or a group NR, in which R is hydrogen or an optionally substituted C1-10 alkyl; Y represents an oxygen or a sulfur atom; and Z represents an oxygen atom, a sulfur atom or an optionally substituted C1-10 alkyl group).

Preferred moieties of formula (III) are those in which X is oxygen or sulfur, preferably oxygen. Where X is a group NR, R is preferably hydrogen. Y is preferably oxygen. Z is preferably an oxygen or sulfur atom or a methyl group, particularly preferably an oxygen atom.

The preferred sulfur-based nucleophile is thiophosphate although other sulfur-based nucleophiles described are also of utility, for example thiophosphoramidates.

Particularly preferably, the sulfur-containing nucleophiles described herein are connected to the polynucleotide through a linker group. The linker may be a carbon-containing chain such as those of formula $(CH_2)n$ wherein "n" is from 1 to about 1500, for example less than about 1000, preferably less than 100, e.g. from 2-50, particularly 5-25. However, a variety of other linkers may be employed with the only restriction placed on their structures being that the linkers are stable under conditions under which the polynucleotides are intended to be used subsequently, e.g. conditions used in DNA sequencing.

Linkers which do not consist of only carbon atoms may also be used. Such linkers include polyethylene glycol (PEG) having a general formula of $(CH_2—CH_2—O)_m$, wherein m is from about 1 to 600, preferably less than about 500.

Linkers formed primarily from chains of carbon atoms and from PEG may be modified so as to contain functional groups which interrupt the chains. Examples of such groups include ketones, esters, amines, amides, ethers, thioethers, sulfoxides, sulfones. Separately or in combination with the presence of such functional groups may be employed alkene, alkyne, aromatic or heteroaromatic moieties, or cyclic aliphatic moieties (e.g. cyclohexyl). Cyclohexyl or phenyl rings may, for example, be connected to a PEG or $(CH_2)_n$ chain through their 1- and 4-positions.

Examples of appropriately modified linkers are those of formula $(CH_2)_n$ (wherein n is as defined above) and in which one or more $CH_2$ units are replaced with functional groups). Thus, one or more $CH_2$ units may be exchanged for an oxygen to form an ether, or for a $SO_2$ to form a sulfone etc. One or more $CH_2$ units may be exchanged for an amide moiety or alkene or alkyne unit. In such linkers one or more functional groups may be present; these functional groups may or may not be the same as each other. Linkers of particular interest contain the propargylamino unit attached to the base (e.g. uracil) in a modified nucleotide. Such nucleotides contain the following unit:

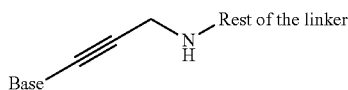

The amino group may be connected to the remainder of the linker by formation of an amide bond.

Modified nucleotides are commercially available, e.g. from the DNA synthesis company Oswel (now Eurogentec Group). Such nucleotides include 3'OH capped nucleotides which may be a basic where a capped linker is attached at the 1'carbon atom or contain a base to which a capped linker is attached. Two such modified nucleotides are Oswel products OSW428 and OSW421:

eroatoms, other linkers may be envisaged which are based on nucleic acids or monosaccharide units (e.g. dextrose). It is also within the scope of this invention to utilise peptides as linkers.

Longer linker moieties (e.g. those containing a chain or more than 100 atoms, particularly those in excess of 500 or even 1000 atoms) serve to position the polynucleotide further away from the solid support. This places the polynucleotide (e.g. DNA) in a environment having a greater resemblance to free solution. This can be beneficial, for example, in enzyme-mediated reactions effected on the polynucleotide. This is because such reactions suffer less from the steric hindrance which manifests itself where the polynucleotide is directly attached to the support or is indirectly attached through a very short linker (such as a linker comprising a chain or only several, e.g. about 1 to 3 carbon atoms).

Where the molecules of interest immobilised on the array are polynucleotides the "linker" may comprise one or more nucleotides which form part of the polynucleotide but which do not participate in any reaction carried out on or with the

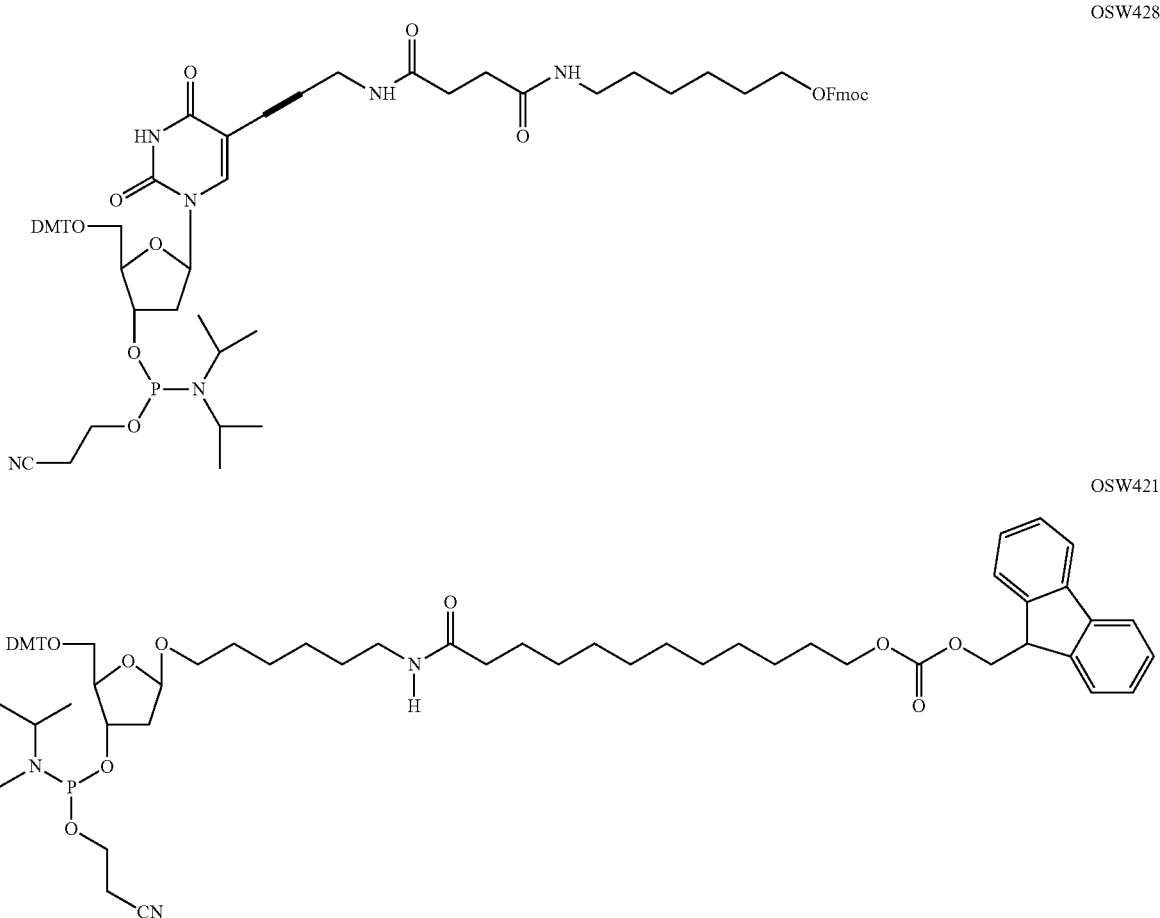

Those skilled in the art will be aware of methods of deprotecting the fluorenylmethoxycarbonyl (Fmoc) group which caps the linker in the nucleotides shown above and for effecting terminal modification, e.g. thiophosphorylation, of the linker.

As an alternative to the linkers described above, which are primarily based on linear chains of saturated carbon atoms, optionally interrupted with unsaturated carbon atoms or hetpolynucleotide (e.g. a hybridisation or amplification reaction). Such nucleotides may be referred to herein as "spacer" polynucleotides. Typically from 1 to 20, more preferably from 1 to 15 or from 1 to 10, and more particularly 2, 3, 4, 5, 6, 7, 8, 9 or 10 spacer nucleotides may be included. Most preferably the polynucleotide will include 10 spacer nucleotides. It is preferred to use polyT spacers, although other nucleotides and combinations thereof can be used. In the most preferred embodiment the polynucleotide will include 10T spacer nucleotides.

Spacer nucleotides are typically included at the 5' ends of polynucleotides which are attached to a suitable support, for example a solid-supported hydrogel, via a linkage with the 5' end of the polynucleotide. Attachment can be achieved through a sulphur-containing nucleophile, such as phosphorothioate, present at the 5' end of the polynucleotide. In the case of arrays based on solid-supported hydrogels, this nucleophile is bound to a "e" group present in the hydrogel. The one or more spacer nucleotides function to space the portions of the polynucleotide that will be "interrogated" and/or subject to further manipulations, such as hybridisation to a second polynucleotide, away from the site of attachment to the solid support. The present inventors have observed that inclusion of spacer nucleotides at the 5' end can markedly improve the performance of hybridisation of complementary polynucleotides to target regions of the immobilised polynucleotides downstream (3') of the spacer nucleotides. Hybridisation yield is observed to increase sharply with polyT spacers of from 2 to 10T nucleotides. When spacer length is increased from 10T up to 20T hybridisation yield begins to decrease. In the most preferred embodiment the polynucleotide will include 10T spacer nucleotides and a 5' phosphorothioate group.

Whilst the use of sulfur nucleophile-containing polynucleotides (particularly thiophosphate-containing) and haloacetamide e groups are preferred to effect attachment of polynucleotides in all aspects of the invention, the skilled person will be able to envisage many other combinations of functionality which will facilitate immobilisation of polynucleotides to the hydrogels described herein. For example, the C group may comprise an activated ester and the polynucleotide may bear an amino group or an oxygen-based nucleophile. Other combinations will be evident to those skilled in the art.

In a particular embodiment the invention provides a method of forming a clustered array on a solid-supported hydrogel by means of a nucleic acid amplification reaction.

Therefore, in a further aspect the invention provides a method of preparing a solid supported hydrogel-based molecular array which is a clustered array of molecules of interest, the method comprising:
(i) reacting polynucleotide molecules with reactive sites present in a solid-supported hydrogel, wherein said polynucleotide molecules are first and second oligonucleotide primers capable of hybridising to a template to be amplified;
(ii) contacting the first oligonucleotide primers attached to the solid-supported hydrogel in step (i) with one or more templates to be amplified under conditions which permit hybridisation of the templates to the oligonucleotide primers, each template comprising at the 3' end a sequence capable of hybridising to the first oligonucleotide primer and at the 5' end a sequence the complement of which is capable of hybridising to a second oligonucleotide primer; and
(iii) performing one or more nucleic acid amplification reactions using the first and second oligonucleotide primers and the template(s), thereby generating a clustered array of molecules of interest.

In this method a solid-supported hydrogel is provided, preferably prepared using the method according to the first aspect of the invention. Oligonucleotide primers are then linked or "grafted" to the hydrogel via reaction with reactive sites present on the hydrogel. This step can be carried out as described above and all preferred features described apply mutatis mutandis to this aspect of the invention. The oligonucleotide primers are preferably attached to the hydrogel via covalent linkage their 5' ends leaving the 3' end of the molecule free to participate in hybridisation to a template polynucleotide and subsequent primer extension by addition of further nucleotides to the free 3' end of the primer. Attachment could also be effected via an internal nucleotide in the primer, provided that this does not prevent the primer from hybridising to a template and subsequent primer extension. The most preferred means of attachment is via 5' phosphorothioate to a hydrogel comprised of polymerised acrylamide and BRAPA.

The precise sequence of the primer oligonucleotides will be dependent on the nature of the template it is intended to amplify. The first and second primers may be of different or identical sequence. The primers can include natural and non-natural bases or any combination thereof, and may also include non-natural backbone linkages such as phosphorothioate. The primer may advantageously' include spacer nucleotides, as described above, in order to optimise the efficiency of subsequent hybridisation to the template polynucleotide. The primer may contain from 1 to 20, more preferably from 1 to 15 or from 1 to 10, and more particularly 2, 3, 4, 5, 6, 7, 8, 9 or 10 spacer nucleotides. Most preferably the primer will include 10 spacer nucleotides. It is preferred to use polyT spacers, although other nucleotides and combinations thereof can be used. In the most preferred embodiment the primer will include 10T spacer nucleotides.

The primer oligonucleotides are grafted onto the surface of the solid-supported hydrogel, effectively forming a surface that is ready to be used for nucleic acid amplification. This approach contrasts with prior art methods for amplification on solid supports, such as that described in WO 98/44151 (schematically illustrated in FIG. 5), wherein a mixture of primers and templates are grafted to the solid surface simultaneously in a single grafting step. In this approach a specific grafting mixture of primers and templates has to be used for each specific template to be amplified. In addition, grafting of long template nucleic acid fragments (>300 bp) is technically difficult. The inventors' approach avoids this problem by removing the need to graft primers and templates simultaneously. In the method of the invention primers are grafted in the absence of template to form a surface that is ready for hybridisation to the template and subsequent amplification.

Following attachment of the primers the solid support is contacted with the template to be amplified under conditions which permit hybridisation between the template and the bound primers. The template is generally added in free solution and suitable hybridisation conditions will be apparent to the skilled reader. Typically hybridisation conditions are 5×SSC at 40° C., following an initial denaturation step.

The template polynucleotide (or a denatured single strand thereof if referring to a template duplex) will include at the 3' end a sequence which permits hybridisation to a first oligonucleotide primer and at the 5' end of the same strand a sequence, the complement of which permits hybridisation to a second oligonucleotide primer (i.e. the sequence of the second primer may be substantially identical to the sequence at the 5' end of the template). The remainder of the template can be any polynucleotide molecule that it is desired to amplify to form a clustered array. Templates may be, for example, fragments of genomic DNA or cDNA that it is desired to sequence. The sequences permitting hybridisation to primers will typically be around 20-25 nucleotides in length. The term "hybridization" encompasses sequence-specific binding between primer and template. Binding of the primer to its cognate sequence in the template can occur under typical conditions used for primer-template annealing in standard PCR.

Following hybridisation of the templates to primers bound to the solid support a nucleic acid amplification reaction can be carried out using the bound primers and the hybridised template. The first step of the amplification reaction will be a primer extension step, in which nucleotides are added to the free 3' ends of the bound primers in order to synthesise complementary strands corresponding to the full length of the template (illustrated schematically in FIG. 6). Subsequent denaturation results in a full-length complementary template strand covalently bound to the solid support. This complementary strand will thus include at its 3' end a sequence which is capable of binding to the second oligonucleotide primer. Further rounds of amplification (analogous to a standard PCR reaction) lead to the formation of clusters or colonies of template molecules bound to the solid support.

DNA amplification on solid supports is a procedure well documented in the literature. A wide range of support types (e.g. microarrays (Huber M. et al. (2001) Anal. Biochem. 299(1), 24-30; Rovera G. (2001) U.S. Pat. No. 6,221,635 B1 20010424), glass beads (Adessi C. et al. (2000) Nucl. Acids Res. 28(20) I e87; Andreadis J. D. et al. (2000) Nucl. Acids Res. 28(2), ed), agarose (Stamm S. et al. (1991) Nucl. Acids Res. 19(6), 1350) or polyacrylamide (Shapero M. H. et al. (2001) Genome Res. 11, 1926-1934; Mitra, R. D. et al. (1999) Nucl. Acids Res. 27(24), e34)) and attachment chemistries (e.g. 5'-thiol oligo on aminosilane slides via heterofunctional crosslinker (Adessi C. et al. (2000) Nucl. Acids Res. 28(20), e87; Andreadis J. D. et al. (2000) Nucl. Acids Res. 28(2), e5), EDC chemistry on NucleoLink™ surface (Sjoroos M. et al. (2001) Clin. Chem. 47 (3), 498-504) or amino silane (Adessi C. et al. (2000) Nucl. Acids Res. 28(20), e87), radical polymerization (Shapero M. H. et al. (2001) Genome Res. 11, 1926-1934; Mitra, R. D. et al. (1999) Nucl. Acids Res. 27(24), e34)) have been described. PCR on polyacrylamide coated glass slides (Shapero et al., ibid) or beads (Mitra et al., ibid) has also been reported. In both cases, at least one of the primers contains a 5'-acrylamide modification so that the primer is covalently attached to the solid support through copolymerization. The method of Mitra et al. consists in premixing of all reagents necessary to perform the PCR, the primers and a very low concentration of the template, then polymerizing a thin polyacrylamide film onto glass slides. In the method of Shapero et al., the primers are both copolymerized while coating the beads and the template is introduced by hybridization later on.

One of the major drawbacks of both methods is the lack of versatility of the surface because of the introduction of the primers with or without the template during preparation of the surface. Moreover, the primers or the template can be potentially damaged by the free radicals generated during the polyacrylamide polymerization.

Figure 5:
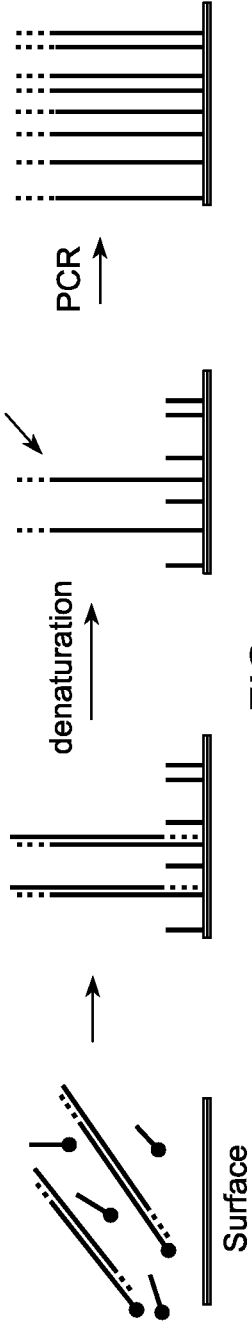
FIG. 5 is a schematic illustration of a prior art method of solid-phase amplification in which a mixture of oligonucleotide primers and template strands are simultaneously grafted onto a solid support.
Figure 5:
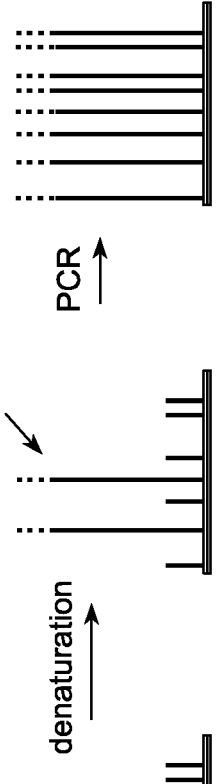

WO 98/44151 describes the use of a hybridisation technique of a template to a primer followed by a chain extension and then replication by PCR to generate colonies or clusters of immobilised nucleic acids on a solid support. The cluster technology as described in WO 98/44151 involves a grafting step that consists of immobilizing simultaneously both primers and templates on a carboxylated surface using standard coupling (EDC) chemistry. This attachment is covalent and has to be done using a specific reaction mixture for every template used. The strategy used is illustrated in FIG. 5.

Figure 6:
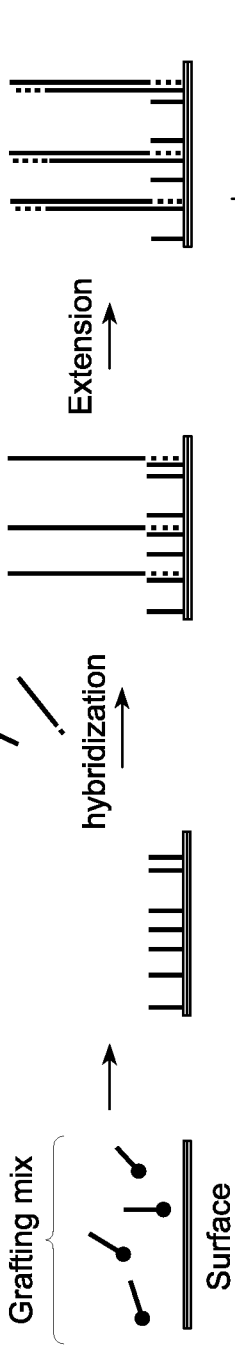
FIG. 6 is a schematic illustration of a method of solid-phase amplification according to the invention in which oligonucleotide primers are first grafted onto a solid support and then hybridised to template strands.
Figure 6:
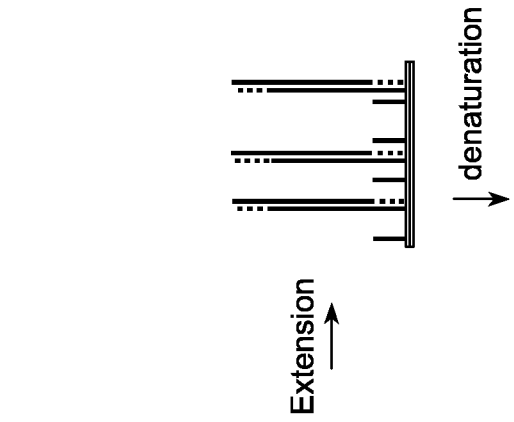
Figure 6:
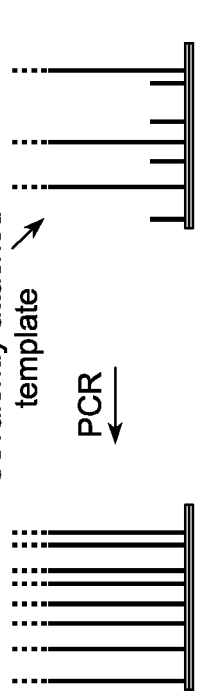

The inventors' approach involves an initial step of preparing the surface of the solid support, followed by covalent attachment (grafting) of primers to generate a surface ready for use in PCR. The PCR template may then be hybridised to attached primers immediately prior to the PCR reaction. The PCR reaction thus begins with an initial primer extension step rather than template denaturation. This approach is illustrated in FIG. 6.

Uses of Arrays Prepared According to the Invention

Once formed, arrays prepared according to the invention may be used in essentially any method of analysis which requires interrogation of molecules of interest on the array or of molecules bound to molecules of interest on the array. In this context, molecules "bound" to molecules of interest on the array includes complementary polynucleotide strands hybridised to polynucleotides bound on the array. By way of example, the arrays may be used to determine the properties or identities of cognate molecules. Typically, interactions between biological or chemical molecules with molecules of interest bound on the arrays are carried out in solution. In preferred embodiments the arrays may be used in procedures to determine the sequence of polynucleotides on the array, and also in the identification and/or scoring of single nucleotide polymorphisms, gene expression analysis, etc.

In particular, the arrays may be used in assays which rely on the detection of fluorescent labels to obtain information on the arrayed molecules, typically arrayed polynucleotides. The arrays are particularly suitable for use in multi-step assays. The arrays may be used in conventional techniques for obtaining genetic sequence information. Many of these techniques rely on the stepwise identification of suitably labelled nucleotides, referred to in U.S. Pat. No. 5,654,413 as "single base" sequencing methods or "sequencing-by-synthesis".

In an embodiment of the invention, the sequence of a target polynucleotide is determined in a similar manner to that described in U.S. Pat. No. 5,654,413, by detecting the incorporation of one or more nucleotides into a nascent strand complementary to the target polynucleotide to be sequenced through the detection of fluorescent label(s) attached to the incorporated nucleotide(s). Sequencing of the target polynucleotide is primed with a suitable primer (or prepared as a hairpin construct which will contain the primer as part of the hairpin), and the nascent chain is extended in a stepwise manner by addition of nucleotides to the 3' end of the primer in a polymerase-catalysed reaction.

In preferred embodiments each of the different nucleotides (A, T, G and C) is labelled with a unique fluorophore which acts as a blocking group at the 3' position to prevent uncontrolled polymerisation. The polymerase enzyme incorporates a nucleotide into the nascent chain complementary to the target polynucleotide, and the blocking group prevents further incorporation of nucleotides. The array surface is then cleared of unincorporated nucleotides and each incorporated nucleotide is "read" optically by suitable means, such as a charge-coupled device using laser excitation and filters. The 3'-blocking group is then removed (deprotected), to expose the nascent chain for further nucleotide incorporation.

Similarly, U.S. Pat. No. 5,302,509 discloses a method to sequence polynucleotides immobilised on a solid support. The method relies on the incorporation of fluorescently-labelled, 3'-blocked nucleotides A, G, C and T into a growing strand complementary to the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur.

In the case of single molecule arrays, because the array consists of distinct optically resolvable polynucleotides, each target polynucleotide will generate a series of distinct signals as the fluorescent events are detected. The sequence of the target polynucleotide is inferred from the order of addition of nucleotides in the complementary strand following conventional rules of base-pairing.

The term "individually resolved by optical microscopy" is used herein to indicate that, when visualised, it is possible to distinguish at least one polynucleotide on the array from its neighbouring polynucleotides using optical microscopy methods available in the art. Visualisation may be effected by the use of reporter labels, e.g., fluorophores, the signal of which is individually resolved.

Other suitable sequencing procedures will be apparent to the skilled person. In particular, the sequencing method may rely on the degradation of the arrayed polynucleotides, the degradation products being characterised to determine the sequence.

An example of a suitable degradation technique is disclosed in WO95/20053, whereby bases on a polynucleotide are removed sequentially, a predetermined number at a time, through the use of labelled adaptors specific for the bases, and a defined exonuclease cleavage.

A consequence of sequencing using non-destructive methods is that it is possible to form a spatially addressable array for further characterisation studies, and therefore non-destructive sequencing may be preferred. In this context, the term "spatially addressable" is used herein to describe how different molecules may be identified on the basis of their position on an array.

In the case that the target polynucleotide fragments are generated via restriction digest of genomic DNA, the recognition sequence of the restriction or other nuclease enzyme will provide 4, 6, 8 bases or more of known sequence (dependent on the enzyme). Further sequencing of between 10 and 20 bases on the array should provide sufficient overall sequence information to place that stretch of DNA into unique context with a total human genome sequence, thus enabling the sequence information to be used for genotyping and more specifically single nucleotide polymorphism (SNP) scoring.

The sequencing method that is used to characterise the bound target may be any known in the art that measures the sequential incorporation of bases onto an extending strand. A suitable technique is disclosed in U.S. Pat. No. 5,302,509 requiring the monitoring of sequential incorporation of fluorescently-labelled bases onto a complement using the polymerase reaction. Alternatives will be apparent to the skilled person. Suitable reagents, including fluorescently-labelled nucleotides will be apparent to the skilled person.

Thus the devices into which the arrays of this invention may be incorporated include, for example, a sequencing machine or genetic analysis machine.

In the case of single molecule arrays the single polynucleotides immobilised onto the surface of a solid support should be capable of being resolved by optical means. This means that, within the resolvable area of the particular imaging device used, there must be one or more distinct signals, each representing one polynucleotide. Typically, the polynucleotides of the array are resolved using a single molecule fluorescence microscope equipped with a sensitive detector, e.g., a charge-coupled device (CCD). Each polynucleotide of the array may be imaged simultaneously or, by scanning the array, a fast sequential analysis can be performed.

The extent of separation between the individual polynucleotides on the array will be determined, in part, by the particular technique used to resolve the individual polynucleotide. Apparatus used to image molecular arrays are known to those skilled in the art. For example, a confocal scanning microscope may be used to scan the surface of the array with a laser to image directly a fluorophore incorporated on the individual polynucleotide by fluorescence. Alternatively, a sensitive 2-D detector, such as a charge-coupled device, can be used to provide a 2-D image representing the individual polynucleotides on the array.

"Resolving" single polynucleotides on the array with a 2-D detector can be done if, at 100× magnification, adjacent polynucleotides are separated by a distance of approximately at least 250 nm, preferably at least 300 nm and more preferably at least 350 nm. It will be appreciated that these distances are dependent on magnification, and that other values can be determined accordingly, by one of ordinary skill in the art.

Other techniques such as scanning near-field optical microscopy (SNOM) are available which are capable of greater optical resolution, thereby permitting more dense arrays to be used. For example, using SNOM, adjacent polynucleotides may be separated by a distance of less than 100 nm, e.g., 10 nm. For a description of scanning near-field optical microscopy, see Moyer et al., Laser Focus World (1993) 29 (10).

An additional technique that may be used is surface-specific total internal reflection fluorescence microscopy (TIRFM) see, for example, Vale et al., Nature (1996) 380: 451-453). Using this technique, it is possible to achieve widefield imaging (up to 100×100 µm) with single molecule sensitivity. This may allow arrays of greater than $10^7$ resolvable polynucleotides per $cm^2$ to be used.

Additionally, the techniques of scanning tunnelling microscopy (Binnig et al., *Helvetica Physica Acta* (1982) 55:726-735) and atomic force microscopy (Hansma et al., *Ann. Rev. Biophys. Biomol. Struct.* (1994) 23:115-139) are suitable for imaging the arrays of the present invention. Other devices which do not rely on microscopy may also be used, provided that they are capable of imaging within discrete areas on a solid support.

Once sequenced, the spatially addressed arrays may be used in a variety of procedures which require the characterisation of individual molecules from heterogeneous populations.

Polynucleotides bound on clustered arrays may also be used as templates for "sequencing-by-synthesis" reactions in which one or more nucleotides are successively incorporated into growing strands complementary to the target polynucleotides to be sequenced and the identity of the base(s} added in one or more of the nucleotide incorporation steps is determined. Again sequencing requires a suitable primer complementary to the template which can serve as an initiation point for the addition of further nucleotides in the sequencing reaction. The sequence of the bound polynucleotide is inferred from the identity of the incorporated nucleotides following conventional base-pairing rules. Methods for nucleic acid sequencing on clustered arrays or nucleic acid "colonies" are described, for example, in WO 98/44152, WO 98/44151, WO 00/18957 and WO 03/074734.

The invention may be understood with reference to the following examples which are to be understood as illustrative, and not limiting, of the present invention.

Preparation 1: Synthesis of N-(5-bromoacetamidylpentyl) acrylamide (BRAPA)

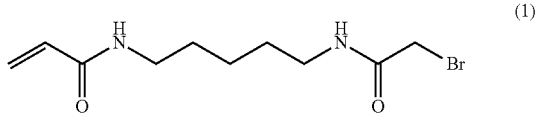
(1)

N-Boc-1,5-diaminopentane toluene sulfonic acid was obtained from Novabiochem. The bromoacetyl chloride and acryloyl chloride were obtained from Fluka. All other reagents were Aldrich products.

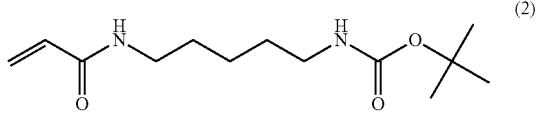 [SMILES: C=CC(=O)NCCCCCNC(=O)OC(C)(C)C]
(2)

To a stirred suspension of N-Boc-1,5-diaminopentane toluene sulfonic acid (5.2 g, 13.88 mmol) and triethylamine (4.83 ml, 2.5 eq) in THF (120 ml) at 0° C. was added acryloyl chloride (1.13 ml, 1 eq) through a pressure equalized dropping funnel over a one hour period. The reaction mixture was then stirred at room temperature and the progress of the reaction checked by TLC (petroleum ether:ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product 2 as a beige solid. $^1$H NMR (400 MHz, d$_6$-DMSO): 1.20 1.22 (m, 2H, CH2), 1.29-1.43 (m, 13H, tBu, 2×CH$_2$), 2.86 (q, 2H, J=6.8 Hz and 12.9 HZ, CH$_2$), 3.07 (q, 2H, J=6.8 Hz and 12.9 Hz, CH$_2$), 5.53 (dd, 1H, J=2.3 Hz and 10.1 Hz, CH), 6.05 (dd, 1H, J=2.3 Hz and 17.2 Hz, CH), 6.20 (dd, IH, J=10.1 Hz and 17.2 HZ, CH), 6.77 (t, 1H, J=5.3 Hz, NH), 8.04 (bs, 1H, NH). Mass (electrospray+) calculated for C$_{13}$H$_{24}$N$_2$O$_3$ 256. found 279 (256+Na$^+$).

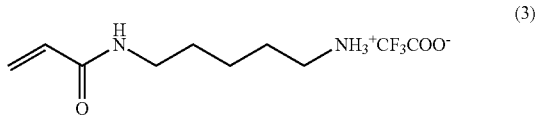
(3)

Product 2 (2.56 g, 10 mmol) was dissolved in trifluoroacetic acid:dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product 3 was obtained as a white powder (2.43 g, 9 mmol, 90%). $^1$H NMR (400 MHz, D20): 1.29-1.40 (m, 2H, CH2), 1.52 (quint., 2H, J=7.1 Hz, CH2), 1.61 (quint., 2H, J=7.7 Hz, CH2), 2.92 (t, 2H, J=7.6 Hz, CH2), 3.21 (t, 2H, J=6.8 Hz, CH2), 5.68 (dd, 1H, J=1.5 Hz and 10.1 Hz, CH), 6.10 (dd, 1H, J=1.5 Hz and 17.2 Hz, CH), 6.20 (dd, 1H, J 10.1 Hz and 17.2 Hz, CH). Mass (electrospray+) calculated for C$_8$H$_{16}$N$_2$O 156. found 179 (156+Na$^+$).

To a suspension of product 3 (6.12 g, 22.64 mmol) and triethylamine (6.94 ml, 2.2 eq) in THF (120 ml) was added bromoacetyl chloride (2.07 ml, 1.1 eq), through a pressure equalized dropping funnel, over a one hour period and at −60° C. (cardice and isopropanol bath in a dewar). The reaction mixture was then stirred at room temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product 1 (BRAPA) were obtained as a white powder. A further recrystallization performed in petroleum ether:ethyl acetate gave 3 g of the product 1. $^1$H NMR (400 MHz, d$_6$-DMSO): 1.21-1.30 (m, 2H, CH2), 1.34-1.48 (m, 4H, 2×CH$_2$), 3.02-3.12 (m, 4H, 2×CH2), 3.81 (s, 2H, CH2), 5.56 (d, IH, J=9.85 Hz, CH), 6.07 (d, IH, J=16.9 Hz, CH), 6.20 (dd, 1H, J=10.1 Hz and 16.9 Hz, CH), 8.07 (bs, IH, NH), 8.27 (bs, IH, NH). Mass (electrospray+) calculated for C$_{10}$H$_{17}$BrN$_2$O$_2$ 276 or 278. found 279 (278+H$^+$), 299 (276+Na$^+$).

Preparation 2: Preparation of Glass Support

A: Cleaning of Glass Slides—

The glass slides used for the preparation of the hydrogel surfaces were cleaned using the following in-house protocol: the slides were sequentially incubated in Decon™, 1M aqueous sodium hydroxide and finally 0.1 M hydrochloric acid (aq). After each step, the slides were sonicated in MilliQ H20. The cleaned slides were stored in ethanol.

B: Binder Silanization of the Glass Slides (Optional)—

The cleaned glass slides were baked at 120° C. for two hours prior to silanization. After cooling down in a dessicator filled with argon, the slides were incubated at room temperature in a 2% v/v solution of either 3-(trimethoxylsilyl)propyl methacrylate or (3-acryloxypropyl)trimethoxy silane in toluene HPLC grade. The slides were then rinsed carefully with toluene and cured for two hours at 120° C. The silanized slides were stored in a dessicator filled with argon.

Preparation 3: Preparation of the Polymerisation Mixture

Acrylamide (Purity 99+%, 0.4 g) was dissolved in MilliQ H$_2$0 (10 mls) (Solution I). Potassium or ammonium persulfate (0.25 g) was dissolved in MilliQ H20 (5 ml) (Solution II). N-(5-bromoacetamidylpentyl)acrylamide (BRAPA) (33 mg) was dissolved in DMF (330 pI) (Solution III).

Solution I was degassed 10 minutes with argon. Solution III was added to solution I.

EXAMPLE 1

Synthesis of Polyacrylamide-Based Surface

Application of the Polyacrylamide Hydrogel to the Glass Slides

Method I—

Two slides (optionally silanised) were assembled with a silicon gasket in between to form a polymerisation cell. The slides and the gasket were held together with binder clips. Polymerisation mixture (800 pI) was injected in each polymerisation cell. The polymerisation proceeded at room temperature' for 1.5 hr. The polymerisation cells were then disassembled and the slides washed thoroughly under running MilliQ H20. The slides were then dried and stored under argon.

Method II—

Slides (optionally silanised) were put into a clean coplin jar. The polymerisation mixture was poured into the jar to cover the slides. The polymerisation proceeded at room temperature for 1.5 hr. The slides were then removed from the coplin jar one by one and rinsed under running MilliQ $H_2O$. The slides were then introduced in clean plastic vials containing MilliQ H20 and vortexed for 20 seconds. The slides were rinsed with running MilliQ H20, dried and stored under argon.

EXAMPLE 2

Immobilisation of Polynucleotides on Polyacrylamide Surfaces

The following constitutes representative procedures for the immobilisation of 5'-phosphorothioate-modified polynucleotides to the new surface. Oligos with a 3'-fluorescent label are typically used for appraising fundamental surface characteristics.

A: Bulk Application (Suitable for Microarrays)

Polynucleotide (1 µM) in the printing buffer (potassium phosphate 100 mM, pH 7) was applied to the surface as 1 µl drops. The slide was then placed in a humid chamber at room temperature for 1 hour. The printed slide was then rinsed with MilliQ $H_2O$ and vortexed in hot washing buffer (Tris HCl 10 mM, EDTA 10 mM, pH 8 (at 80-90° C.)). The printed slide was finally rinsed with MilliQ H20, dried under a flow of argon and stored in the dark before imaging.

To immobilise polynucleotides over a large area, a gasket was placed onto the slide, the polynucleotide solution injected into the chamber formed and a cover slip placed over the gasket. The slide was then incubated for 1 h at room temperature in a humid chamber and processed as described above.

B: Single Molecule Array Application

The coated slide was fitted into a custom-made flow cell. Polynucleotide (400 µl, 0.1 to 10 nM) in the printing buffer was injected into the cell. The concentration of polynucleotide is chosen to achieve a precise single molecule density of polynucleotides on the surface. The cell was incubated in the dark at room temperature for 1 h. The printed surface was then washed by sequentially injecting printing buffer (20 ml), hot washing buffer (20 ml, 80-90° C.) and finally MilliQ $H_2O$ (20 ml).

EXAMPLE 3

Thermal Stability of the Immobilised Polynucleotides

A. Bulk Application (Suitable for Microarrays)—

A printed slide was imaged with a fluorescence scanner in the presence of a fluorescence reference control slide containing attached Cy3 dye. The printed slide was then incubated in a jar containing printing buffer at a preset temperature in the dark. The slide was imaged at regular intervals and the fluorescence intensity recorded. The fluorescence intensity of a spot is proportional to the amount of polynucleotide immobilised on that area. A plot of the variation of the fluorescence intensity with time gave a stability profile for attached polynucleotide on the polyacrylamide surface.

B: Single Molecule Array Application—

A slide was printed in a flow cell as described above. Printing buffer is injected through the cell at a rate of 1 ml/min, at a preset temperature, and the slide imaged at regular intervals using a custom-made total internal reflection fluorimeter instrument. The stability profile of the single molecule array is obtained by plotting the variation of the number of single molecules counted in a specific area with time.

EXAMPLE 4

Evaluation of Surface Passivation Towards Nucleotide Sticking at SMA Level

A coated slide was fitted into a custom-made flow cell. The cell was flushed with MilliQ $H_2O$ (10 ml) then phosphate printing buffer (0.1 M, pH 7.0) and then incubated for 30 minutes at room temperature. This procedure constituted a mock DNA couple to the surface. The cell was flushed with MilliQ $H_2O$ (10 ml), hot TE buffer (10 ml, 10 mM Tris.HCl, 10 mM EDTA, pH 8.0) then MilliQ $H_2O$ (10 ml). The slide was then imaged using a custom-made total internal reflection fluorimeter instrument to give a fluorescent background reading. The cell was then flushed with enzymology buffer (10 ml, 50 mM Tris.HCl, 4 mM $MgSO_4$, 0.2 mM $MnCl_2$, 0.05% Tween 20, pH 8.0). A solution of fluorescently-labelled nucleotide (400 µl, 0.2 to 2 µM in enzymology buffer) was then injected into the cell and the cell incubated at a preset temperature for 30 minutes. The cell was flushed with wash buffer (10 ml, 50 mM Tris.HCl, 4 mM $MgSO_4$, 0.05% Tween 20, pH 8.0), high salt buffer (10 ml, 50 mM Tris.HCl, 1M NaCl, 4 mM $MgCl_2$, 0.05% Tween 20, pH 8.0), TE buffer (10 ml, composition as above) and MilliQ $H_2O$ (10 ml). The slide was then imaged using a custom-made total internal reflection fluorimeter instrument to determine the level of nucleotide sticking to the surface.

EXAMPLE 5

Evaluation of Enzymology on Surface Immobilised Hairpin DNA

A: Single Molecule Array Application—

A coated slide was fitted into a custom-made flow cell. A solution of self-priming DNA hairpin (200 µl, 1 nM, 0.1M KPi, pH 7.0) was then injected into the flow cell and the cell incubated for 1 hr at room temperature. The cell was then flushed with boiling TE buffer (20 ml, 10 mM Tris.HCl, 10 mM EDTA, pH 8.0) and MilliQ $H_2O$ (20 ml). The slide was then imaged using a custom-made total internal reflection fluorimeter instrument to give a fluorescent background reading. The flow cell was then flushed with wash buffer (20 ml, 50 mM Tris.HCl, 4 mM $MgSO_4$, 0.05% Tween 20, pH 8.0) and then enzymology mix (2×100 µl, 0.2 mM fluorescently-labelled nucleotide, 5 µg/ml DNA polymerase, 50 mM Tris.HCl, 4 mM $MgSO_4$, 0.4 mM $MnCl_2$, 0.05% Tween 20, pH 8.0) was injected into the flow cell. The flow cell was incubated at 45° C. for 30 minutes. The flow cell was then flushed at a flow rate of 0.5 ml/s with wash buffer (20 ml, 50 mM Tris.HCl, 4 mM $MgSO_4$, 0.05% Tween 20, pH 8.0), high salt wash buffer (20 ml, 50 mM Tris.HCl, 1 M NaCl, 4 mM $MgSO_4$, 0.05% Tween 20, pH 8.0), TE buffer (20 ml, 10 mM Tris.HCl, 10 mM EDTA, pH 8.0) and milliQ $H_2O$ (20 ml). The slide was then imaged using a custom-made total internal reflection fluorimeter instrument to determine the level of enzyme incorporation of the fluorescently-labelled nucleotide into the hairpin.

EXAMPLE 6

Preparation of a Polyelectrolyte-Treated Fused Silica-Supported Hydrogel and a Demonstration that it is More Passive Towards Functionalised Labelled Nucleotides when Compared to a Non-Treated Control A: A polyacrylamide-based glass-supported hydrogel is prepared as described in Example 1.

B: Pretreatment with polyallylamine hydrochloride followed by polyacrylic acid. Treatment of a polyacrylamide hydrogel comprising 1 mol % BRAPA, as described in Part A, is effected by contacting the hydrogel with a solution of polyallylamine hydrochloride (2 mg/ml) MilliQ $H_2O$ at pH 8. Contacting is effected for 30 min at room temperature after which the solution is treated with polyacrylic acid (2 mg/ml MilliQ $H_2O$ at pH 8.2). The solution is incubated for 30 min at room temperature followed by treatment with MilliQ $H_2O$. The surface treated with the two layers of polyelectrolyte demonstrates a reduction in sticking of fluorescently functionalised nucleotides when compared to a control hydrogel surface not treated with the polyelectrolytes.

EXAMPLE 7

Demonstration that of a Poly(Ethylene Glycol)-Treated Fused Silica-Supported Hydrogel is More Passive Towards Functionalised Labelled Nucleotides when Compared to a Non-Treated Control Example 6 was repeated except that instead of treatment with polyallylamine hydrochloride following by polyacrylic acid, the hydrogel prepared as in example 1 is treated with poly(ethylene glycol) 8000 (Sigma). The surface treated with the poly(ethylene glycol) 8000 demonstrates a reduction in sticking of fluorescently functionalised nucleotides when compared to a control hydrogel surface not treated with the poly(ethylene glycol) 8000.

EXAMPLE 8

Demonstration that Treatment of a Polyelectrolyte- or Poly(Ethylene Glycol)-Treated Fused Silica-Supported Hydrogel-Based Molecular Array is More Passive Towards Functionalised Labelled Nucleotides when Compared to a Non-Treated Control Examples 6 and 7 are repeated except that instead of applying the polyelectrolytes or poly(ethylene glycol) to a fused silica-supported hydrogel as such, instead an array of polynucleotides is treated and the arrays so modified used in sequencing reactions with fluorescently labelled nucleotides. The surfaces treated with either the two layers of polyelectrolyte, or the poly(ethylene glycol) 8000, demonstrate a reduction in sticking of fluorescently functionalised nucleotides when compared to a control hydrogel surfaces not so treated.

EXAMPLE 9

Preparation of Plastics-Supported Hydrogel

Plastic substrates were obtained from Amic and were cleaned with Decon 90 overnight. These were poly(methyl methacrylate) (Amic PMMA), and cyclic olefin 1060 and 1420 plastics (Amic (COP) 1060 and Amic (COP) 1420). The next day they were rinsed extensively with MilliQ water and dried. A 2% w/v acrylamide solution was made up by dissolving 1.3 g acrylamide in 65 ml of MilliQ water. This solution was then purged with argon for 15 minutes to remove oxygen, which may inhibit the polymerisation reaction. BRAPA (107 mg) was then dissolved with 1.07 ml of dimethylformamide (DMF) and added to the degassed acrylamide solution. After mixing, 75 µl of TEMED catalyst was added to the acrylamide/BRAPA solution. Then polymerisation was started by adding 0.65 ml of a 0.05 g/ml solution of potassium persulfate initiator to the acrylamide/BRAPA/TEMED solution. The acrylamide/BRAPA/TEMED/persulfate solution was quickly mixed and added to a coplin jar containing the clean dry plastic (and glass) substrates. After 90 minutes the slides were removed from the polymerising mixture and rinsed copiously with MilliQ under flow. They were then vortexed 20 seconds in MilliQ and rinsed a second time under flow before being dried with Argon. Slides treated in this way are hereinafter referred to as being slides treated with silane-free acrylamide (SFA) or "support with SFA".

EXAMPLEs 10

Functionalisation of Plastics-Supported Hydrogel

Following slide preparation as described in Example 9, CultureWell coverglass gaskets from GraceBio labs were attached to the slides for 1 hour. 1 phosphorothioate-Cy3-DNA (positive) and 1 µM hydroxyl-Cy3-DNA (negative, control DNA) in 10 µM phosphate buffer pH 7 were then spotted in wells on the plastic (and glass) slides and coupling carried out for 1 hour in a humidity chamber at room temperature (20° C.). Following coupling each slide was rinsed copiously with higher ionic strength 0.10 M phosphate buffer. The gasket was then carefully removed and the slide then vortexed 20 seconds in 10 mM Tris/10 mM EDTA pH 8 buffer. Finally the slide was rinsed with MilliQ water under flow, then dried with argon.

EXAMPLE 11

Detection of Oligonucleotide Functionalisation of Plastics-Supported Hydrogel

Fluorescence scanning was performed on a Typhoon 8600 imager at 550V, 100 µm resolution in the Cy3 channel (532 laser excitation).

The images shown in FIG. 1 show the attempted coupling of positive (PS, phosphorothioate) and negative (OH, hydroxyl control) DNA to Amic PMMA and 1060 and 1420 plastics with and without SFA. As may be seen by comparison of the 1st and 2nd columns of images, a fluorescent signal is only obtained when the plastic has been first coated with SFA. Some non-specific binding of 1 µM hydroxyl DNA is observed but less than in the case of the glass substrate. This suggests that substrate effects are still present despite the presence of SFA coating.

Figure 2:
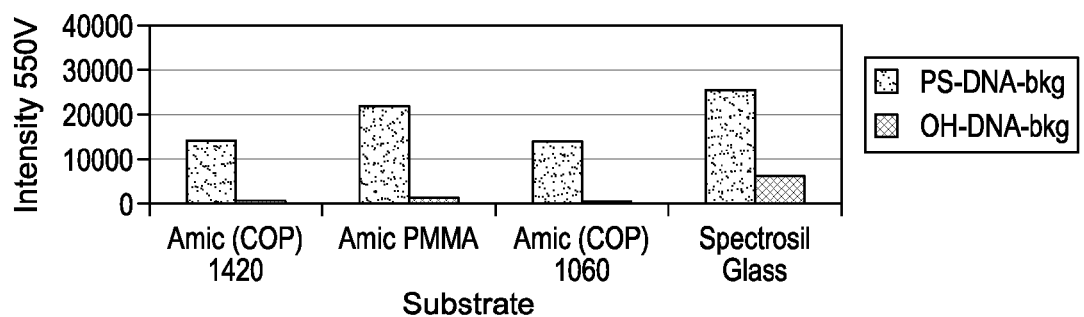
FIG. 2 shows the relative levels of positive signal due to PS-DNA binding versus negative noise from OH-DNA binding resultant from coupling of 1 µM PS-DNA and 1 µM OH-DNA to plastic and fused silica (SPECTRASIL® glass) detected on the surfaces whose preparation is described in Example 10.
Figure 3:
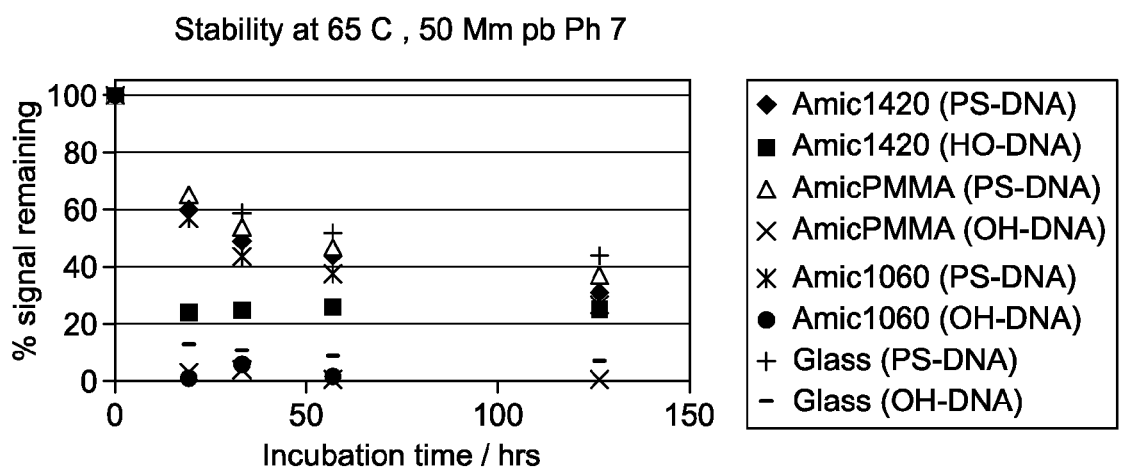
FIG. 3 shows the apparent stability of the specifically adsorbed PS-DNA (in 50 mM phosphate buffer (pH7, 65° C.)) for various plastics materials is approximately the same as that for SPECTRASIL™ glass.

The relative levels of positive signal due to phosphorothioate binding are shown in FIG. 2 along with the measured signal-to-noise values (phosphorothioate DNA: hydroxyl DNA). The graph shown in FIG. 3 shows that the apparent stability of the specifically adsorbed phosphorothioate DNA in 50 mM phosphate buffer pH 7 at 65° C. is essentially the same as that for glass. Approximately 40% of the starting signal is left after 7 days incubation in 50 mM phosphate pH 7 at 65° C. This value is slightly lower than expected for both glass and plastic substrates and is attributed to the fact that the samples were always scanned dry after briefly rinsing with MilliQ water. When dry, the fluorescent dye is greatly affected by environmental conditions particularly ozone levels.

EXAMPLE 12

Further Preparation of Plastics-Supported Hydrogels

Other plastics (e.g. polystyrene) and plastics of the same type but from different suppliers were also tested and hybridisation studies attempted as follows:

Polystyrene from Corning, Zeonex E48R (a cyclic olefin polymer) from Zeon Chemicals Ltd. and poly(methyl methacrylate) from the Technical University of Denmark, as well as Spectrosil glass substrates, were cleaned as described in Example 9. Some clean samples were kept aside while others were coated with SFA as described in Example 9.

1 µM phosphorothioate-Cy3-DNA (positive), 1 µM hydroxyl-Cy3-DNA (negative, control DNA), 1 µM unlabelled P5 primer with a 10T spacer and 1 µM unlabelled P7 primer with a 10T spacer were coupled to substrates as prepared in Example 12, and cleaned but not treated with SFA. Scanning was then performed as described in Example 12. Following scanning hybridisation was carried out using a Texas Red labelled complementary target to the P5 primer (P5') by attaching a square silicone gasket to the substrate then placing another clean (uncoated glass) slide on top to form a cell. An injection of 0.5 µM complementary target in 5× sodium citrate (SSC), 0.1% Tween 20 buffer pH 7 was then made into the space created by the gasket and the cell heated in an oven to 95° C. for 30 minutes. The oven temperature was then switched to 50° C. and the cell allowed to cool for 2 hours. Afterwards the cell was removed and allowed to cool at room temperature for 10 minutes in the dark. The complementary target solution was then removed with a syringe and fresh 5×SSC, 0.1% Tween 20 buffer at room temperature injected, then removed. This washing procedure was repeated 5 further times. The cell was then dismantled and the substrate agitated in a beaker of fresh 5×SSC, 0.1% Tween 20 for 2 minutes. The substrate was then transferred to a beaker containing higher stringency (0.1×SSC, 0.1% Tween 20) and agitated for 2 minutes. This was repeated once more then the substrate dried with argon. The samples were then scanned again this time at 700 V in the Rox channel using 633 nm excitation (100 µm resolution).

Figure 4:
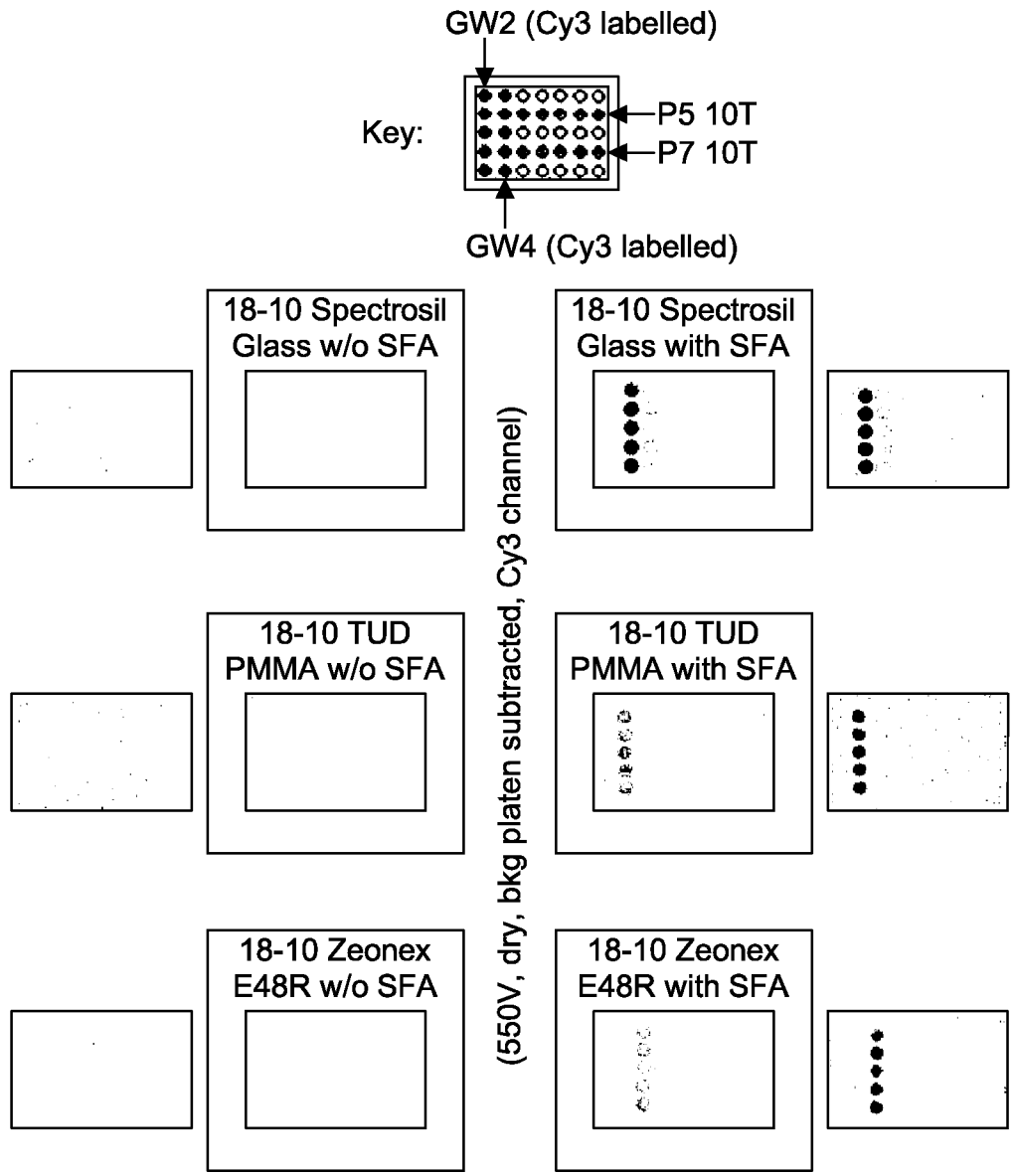
FIG. 4 shows images of the detection of fluorescence from oligonucleotides, immobilised on substrates both according to and not according to the invention, in accordance with Example 13. The improved binding of phosphorothioate-terminated DNA (PS-DNA) over hydroxyl-terminated DNA may be seen.
Figure 4:
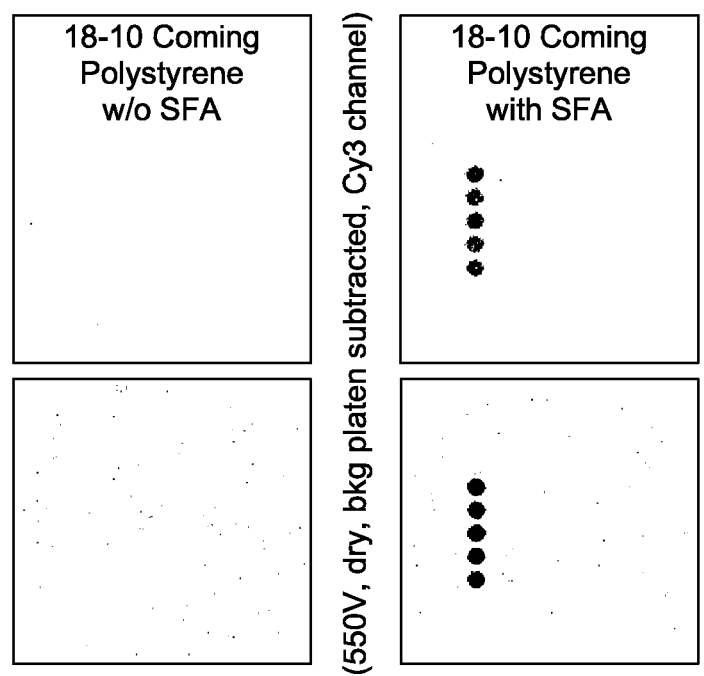
Figure 4:
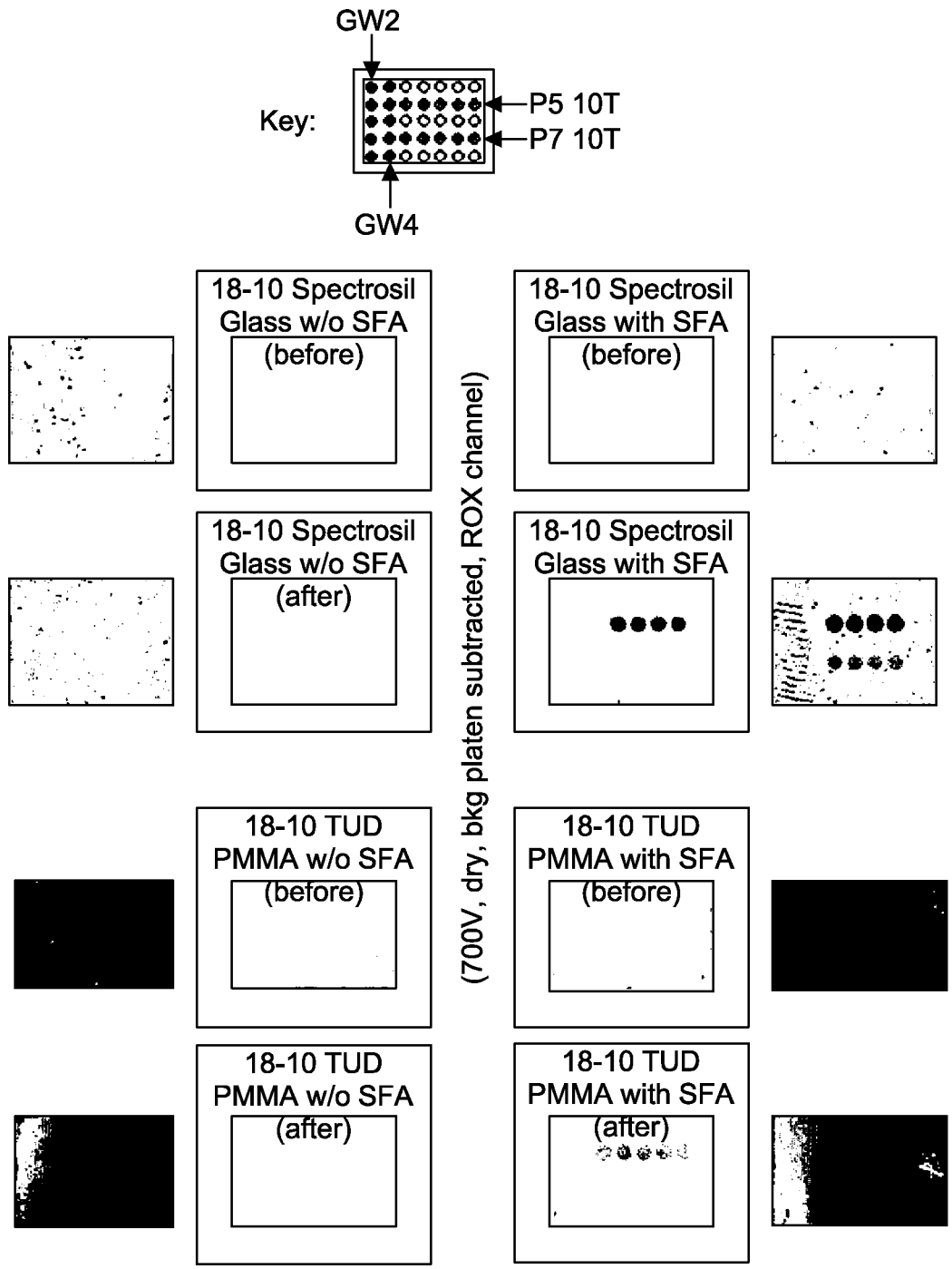
Figure 4:
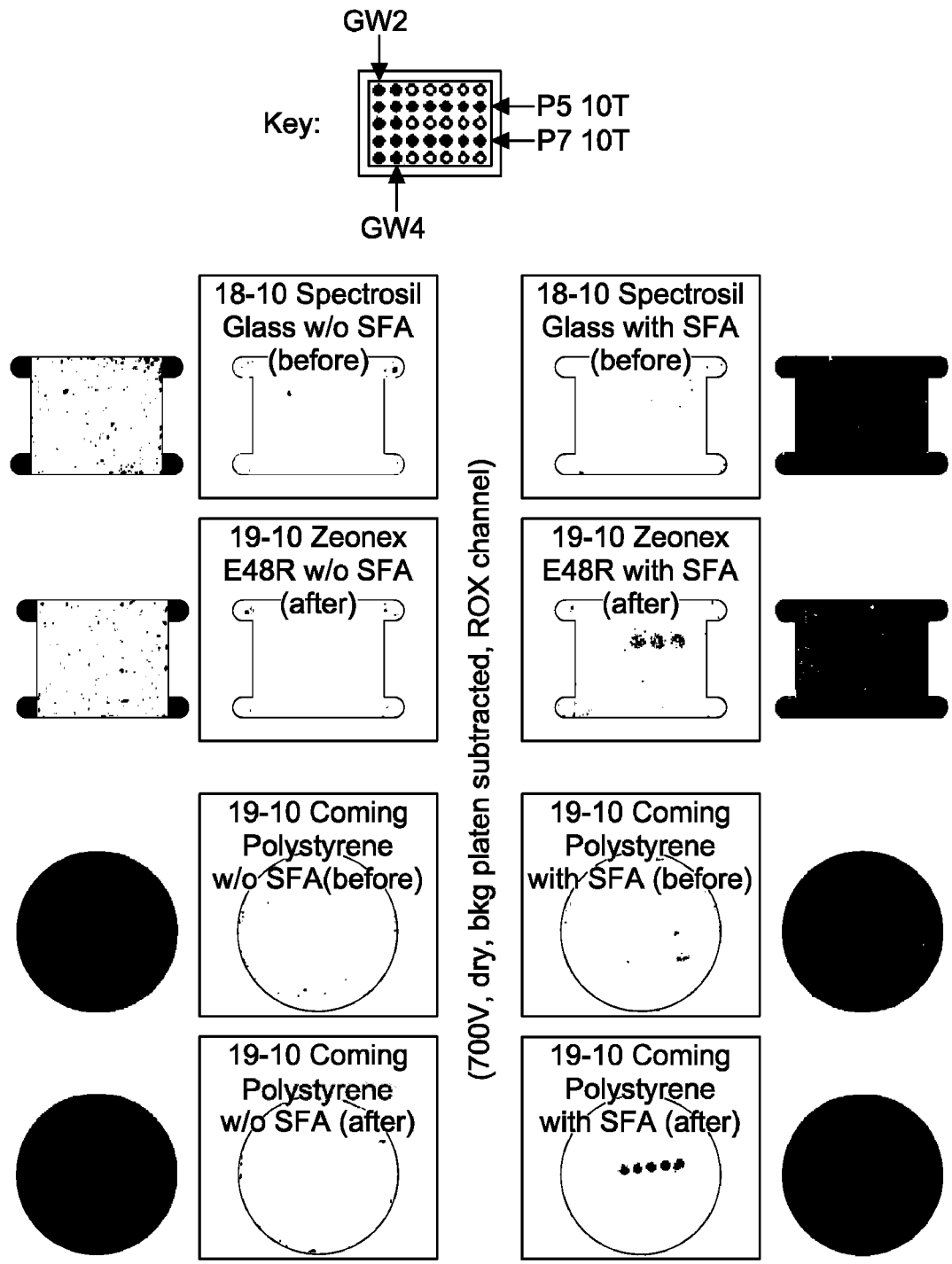

The images shown in FIG. 4 shows below the coupling of the Cy3-labelled phosphorothioate (GW2) and hydroxyl DNA (GW4) to glass and plastic substrates with and without SFA coatings. Again, the same results were obtained (i.e. coupling of phosphorothioate DNA only when SFA is present) although the signal intensities and signal-to-noise ratios vary slightly from before (see graph).

EXAMPLE 13

Formation of Clustered Arrays by Template Hybridisation and PCR

Overview:

The inventors' approach involves an initial step of preparing the surface of the solid support, followed by covalent attachment (grafting) of primers to generate a surface ready for use in PCR. The PCR template may then be hybridised to attached primers immediately prior to the PCR reaction. The PCR reaction thus begins with an initial primer extension step rather than template denaturation. This approach is illustrated in FIG. 6.

Experimental:

The solid supports used in this experiment were 8-channel glass chips such as those provided by Micronit (Twente, Nederland) or IMT (Neuchâtel, Switzerland). However, the experimental conditions and procedures are readily applicable to other solid supports.

Chips were washed as follows: neat Decon for 30 min, milliQ $H_2O$ for 30 min, NaOH 1N for 15 min, milliQ $H_2O$ for 30 min, HCl 0.1N for 15 min, milliQ $H_2O$ for 30 min.

Chips were then coated with polyacrylamide hydrogel as described in Example 1.

5'-phosphorothioate oligonucleotides were grafted onto the surface of the hydrogel in 10 mM phosphate buffer pH7 for 1 h at RT. The following exemplary primers were used:

```
P7 primer with polyT spacer:
                                    (SEQ ID NO: 1)
5'phosphorothioate-TTTTTTTTTTCAAGCAGAAGACGGCATA
CGA-3'

P5 primer with polyT spacer:
                                    (SEQ ID NO: 2)
5'phosphorothioate-TTTTTTTTTTAATGATACGGCGACCACC
GA-3'
```

Primers were used at a concentration of 0.5~M in the grafting solution.

The template used was a fragment of pBluescript T246 containing sequences complementary to the P7/P5 primers shown above. The hybridization procedure began with a heating step in a stringent buffer (95° C. for 5 minutes in TE) to ensure complete denaturation prior to hybridisation of the template. Hybridization was then carried out in 5×SSC, using template diluted to a final concentration of 5 nM. After the hybridization, the chip was washed for 5 minutes with milliQ water to remove salts.

Surface amplification was carried out by thermocycled PCR in an MJ Research thermocycler.

A typical PCR program is as follows:

1-97.5° C. for 0:45
2-X° C. for 1:30
3-73° C. for 1:30
4-Goto 1 [40] times
5-73° C. for 5:00
6-20° C. for 3:00
7-End Since the first step in the amplification reaction is extension of the primers bound to template in the initial hybridisation step the first denaturation and annealing steps of this program were omitted (i.e. the chip was placed on the heating block only when the PCR mix was pumped through the channels and the temperature was 73° C.).

The annealing temperature (X° C., step 2) depends on the primer pair that is used. Experiments have determined an optimal annealing temperature of 57° C. for P5/P7 primers.

For other primer-pairs the optimum annealing temperature can be determined by experiment. The number of PCR cycles may be varied if required.

PCR was carried out in a reaction solution comprising 1×PCR reaction buffer (supplied with the enzyme) 1M betaine, 1.3% DMSO, 200 µM dNTPs and 0.025 U/µL Taq polymerase.

In order to visualise colonies the glass chips were stained with SYBR Green-I in TE buffer (1/10000) and then viewed using an epifluorescence microscope. It was observed that amplified colonies had formed in channels treated as described above, but not in control channels in which the template was added at the primer grafting stage (data not shown).

EXAMPLE 14

Effect of Spacer Length on Polynucleotide Hybridisation

Background:

DNA microarrays may be used to carry out thousands of heterogeneous (solid-liquid interface) hybridisations simultaneously to determine gene expression patterns or to identify genotype. Hybridisation on these arrays depends on a number of factors including probe density (Peterson, A. W. et al. (2001) Nucl. Acids Res. 29, 5163-5168) while kinetic rates and equilibrium binding constants may differ markedly from the solution phase.

Due to steric hindrance and a reduced degree of freedom the proximity to the support surface is a key criterion affecting hybridisation yield (Weiler, J et al. (1997) Nucl. Acids Res. 25, No. 14, 2792-2799). Shchepinov et al., determined that 60 atoms was the optimal spacer length for a hydrophilic PEG-phosphoroamidite synthon spacer (Shchepinov, M. S. et al. (1997) Nucl. Acids Res. 25, 1155-1161). This resulted in a 50-fold increase in hybridisation yield. Above 60 atoms (approx. 10 glycol units) hybridisation yield decreased until at 30 units the yield of hybridisation was the same as that with no spacer at all. Moreover, the yield of hybridisation was affected by the charge density along the spacer while being independent of charge type.

The hybridisation studies outlined below show that it was possible to improve hybridisation yield by incorporating a polyT spacer into the primer. Similar oligoT spacers have been shown previously to produce a 20-fold enhancement of hybridization (Guo, Z. et al. (1994) Nucl. Acids Res. 22, 5456-5465).

Experimental:

(1) Hybridization on a Microplate-Effect of Spacer Modification of Glass with Silane-Free Acrylamide (SFA):

A 96 well, glass bottom, polystyrene microplate was placed into Decon 90 overnight. The next day the microplate was rinsed extensively with MilliQ water, then dried with Argon. The glass surface of each well of the microplate was then coated with silane-free acrylamide (SFA). Briefly, acrylamide was dissolved in water to give a 2% w/v solution and argon then bubbled through this solution for 15 minutes.

82.5 mg of BRAPA (the active monomer) was dissolved in 0.825 ml dimethylformamide (DMF). This solution was then added to 50 ml of acrylamide solution to give a 2 mol % BRAPA solution with respect to acrylamide. After mixing 57.5 µl TEMED was added to the acrylamide/BRAPA solution. A potassium persulfate solution was then prepared by dissolving 0.1 g in 2 ml MilliQ water. 0.5 ml of the initiator solution was then added to the degassed acrylamide/BRAPA/TEMED solution and, after mixing, 0.4 ml of the polymerisation mixture was pipetted into each well of the microplate. Polymerisation was allowed to proceed for 1.5 hours, then the microplate was washed on an automated microplate washer with program AHPEM160. Following washing the plate was dried under argon and stored overnight under vacuum.

Coupling of Oligo Primers to SFA Surface:

The following 4 primers were coupled to the surface at 2.0 µM, 1.0 µM, 0.5 µM and 0.1 µM concentrations from 10 µM phosphate buffer pH 7:

1) P7 primer without polyT spacer:
(SEQ ID NO: 3)
5'phosphorothioate-CAAGCAGAAGACGGCATACGA-3'

2) P7 primer with polyT spacer:
(SEQ ID NO: 1)
5'phosphorothioate-TTTTTTTTTTCAAGCAGAAGACGGCATACGA-3'

3) P5 primer without polyT spacer:
(SEQ ID NO: 4)
5'phosphorothioate-AATGATACGGCGACCACCGA-3'

4) P5 primer with polyT spacer:
(SEQ ID NO: 2)
5'phosphorothioate-TTTTTTTTTTAATGATACGGCGACCACCGA-3'

Coupling was carried out using 0.1 ml oligonucleotide solution for 1 hour in a humid environment at room temperature. Afterwards the microplate was washed with 0.10 M phosphate buffer pH 7 on an automated microplate washer.

Figure 7:
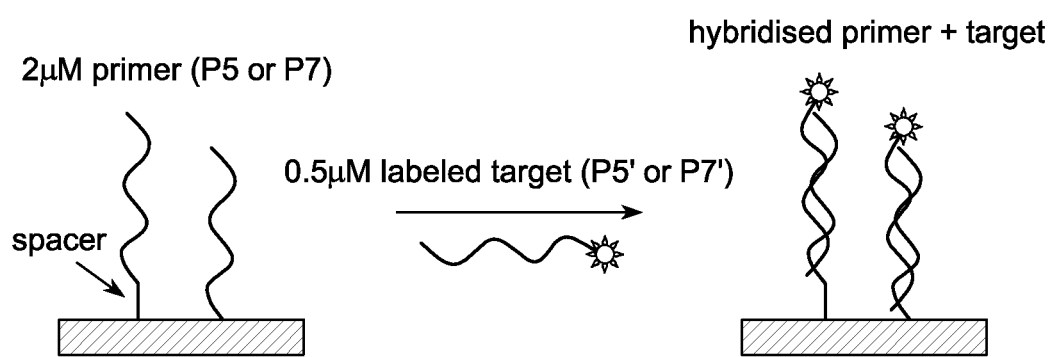
FIG. 7 illustrates the use of spacer nucleotides to improve efficiency of hybridisation between an immobilised polynucleotide primer and a labelled target, according to Example 14.

Hybridisation:

Hybridisation to the primers (FIG. 7) was carried out using the following complementary Texas Red labelled targets:

P5' complementary target to PS sequence:
(SEQ ID NO: 5)
5'Texas Red-TCGGTGGTCGCCGTATCATT-3'

P7' complementary target to P7 sequence:
(SEQ ID NO: 11)
5'Texas Red-TCGTATGCCGTCTTCTGCTTG-3'

The target volume was 0.1 ml and the concentration was 0.5 µM. The target was made up in two different hybridisation buffers and tested. The composition of the TAQ PCR buffer was 1M betaine, 1.3% DMSO, 10 mM Tris, 1.5 mM MgCl$_2$ and 50 mM KCl (pH 9). The other buffer contained 5×SSC (diluted from a 20× stock) and 0.1% (v/v) Tween 20 (pH 7). A special PCR film was used to seal the wells of the microplate and prevent evaporation on heating. The plate was then placed on a PCR block with lid and submitted to the following conditions:

1) 0.5 o/S to 97.5° C.
2) 97.5° c. for 2 mins 30 secs
3) 97.5° c. for 2 sees –0.1° c. per cycle
4) Goto 3, 574 times
5) 40.0° c. for 15 mins
6) End After heating and cooling the plate was washed 15 times using the microplate washer (modified program 'AHPEM170') with 5×SSC, 0.1% v/v Tween 20 pH 7, then 6 times using the same program but with 0.1×SSC, 0.1% v/v Tween 20 pH 7. Following washing the plate was scanned wet under on a Typhoon 9600 imager at 700V with the ROX filter, 633 nm excitation, 200 mM pixel size.

Figure 8A:
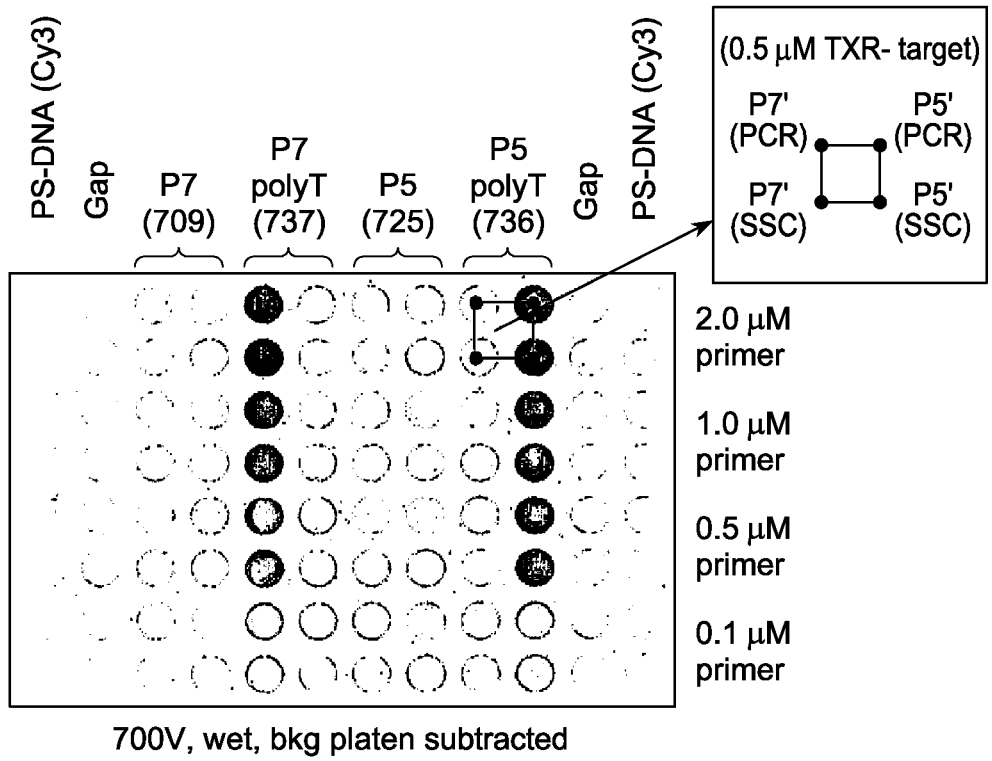
FIGS. 8(a) and 8(b) show the results of hybridisation experiments carried out in microtiter plates between various concentrations of immobilised primers—with and without spacer nucleotides—and target oligonucleotides labelled with Texas red (TXR).
Figure 8B:
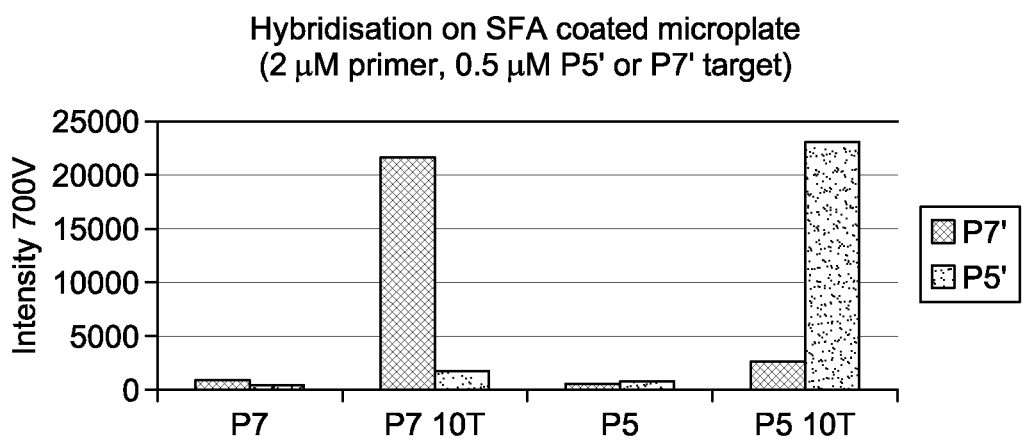

Results:

The results presented in FIG. 8 show a clear improvement in hybridisation signal for both the P5 and P7 primer upon adding a spacer with 10 T bases. Not only is the signal much higher but the signal-to-noise (specific to non-specific hybridisation) also improves immensely.

(2) Hybridization on Typhoon Slides—Effect of Spacer Coupling of Oligo Primers to SFA Surface:

The following 4 primers were coupled to the surface at 1.0 µM concentrations from 10 mM phosphate buffer pH 7:

```
1) P7 primer without polyT spacer:
                                    (SEQ ID NO: 3)
5'phosphorothioate-CAAGCAGAAGACGGCATACGA-3'

2) P7 primer with polyT spacer:
                                    (SEQ ID NO: 1)
5'phosphorothioate-TTTTTTTTTTCAAGCAGAAGACGGCAT
ACGA-3'

3) P5 primer without polyT spacer:
                                    (SEQ ID NO: 4)
5'phosphorothioate-AATGATACGGCGACCACCGA-3'

4) P5 primer with polyT spacer:
                                    (SEQ ID NO: 2)
5'phosphorothioate-TTTTTTTTTTAATGATACGGCGACCAC
CGA-3'
```

Figure 9:
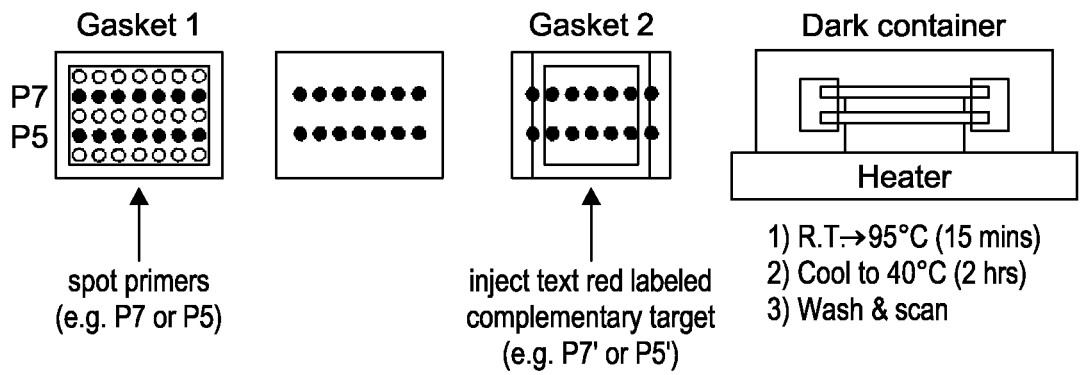
FIG. 9 illustrates experimental set-up for hybridisation experiments described in Example 14.

Coupling was carried out for 1 hour by spotting 7 µl of each oligo into one or more wells created by sticking a Grace Biolab CultureWell coverglass gasket (gasket 1, FIG. 9) onto a Typhoon slide previously modified with 2% acrylamide, 2 mol % BRAPA silane-free acrylamide. During coupling the slides were kept in the dark in a humidity chamber. After coupling the slides were rinsed with 250 ml of 0.1 M phosphate buffer pH 7 from a wash bottle. Then each slide was vortexed 20 seconds in 10 mM/10 mM Tris/EDTA pH 8 buffer, then rinsed with MilliQ water and dried.

Hybridisation:

Hybridisation to the primers (FIG. 7) was carried out using the following complementary Texas Red labelled targets:

```
P5' complementary target to P5 sequence:
                                    (SEQ ID NO: 5)
5'Texas Red-TCGGTGGTCGCCGTATCATT-3'

P7' complementary target to P7 sequence:
                                    (SEQ ID NO: 11)
5' Texas Red-TCGTATGCCGTCTTCTGCTTG-3'
```

A silicone gasket (gasket 2, FIG. 9) was attached to the primer modified slide and a clean glass slide placed on top to create a sealed chamber. Clips were used to ensure sealing. The space created by the gasket was then filled with one of the complementary targets (P5' or P7') then the primer-modified side was placed in contact with an aluminium heating block. A box was placed on top to prevent access of light. The temperature of the aluminium block was increased from room temperature to 95° C. (required 15 minutes). The temperature of the heater was then turned down to 40° C. and the slides allowed to cool to 50° C. (required 2 hours). Once at 50° C. the slide was allowed to cool to room temperature during 10 minutes. The complementary target solution was then removed with a syringe and the inside washed by injection 6× with 5×SSC, 0.1% Tween 20. The gasket, clips and slides were then dismantled and the primer-modified slide rinsed with agitation in a tube containing 5×SSC, 0.1% Tween 20 for 2 minutes. This was repeated then the primer-modified slide was rinsed with O.1×SSC, 0.1% Tween 20, twice for 2 minutes with agitation. The slide was then dried with Argon and scanned dry at 700V as above.

Figure 10:
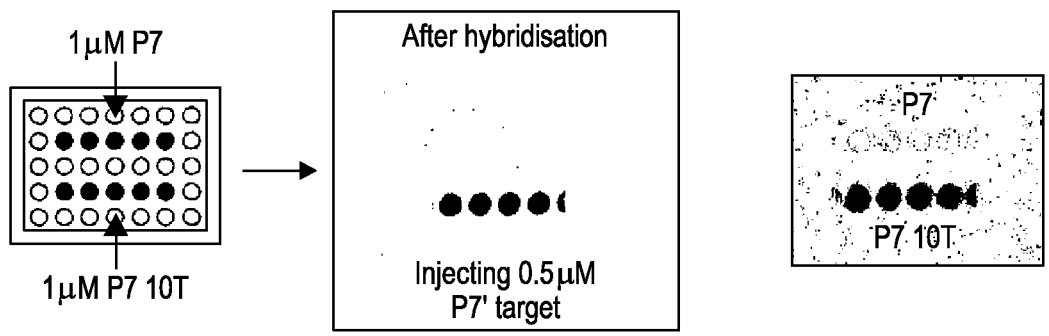
FIG. 10 illustrates experimental set-up and results of hybridisation experiments using various immobilised oligonucleotide primers, with and without spacer nucleotides, and complementary labelled target oligonucleotides.
Figure 10:
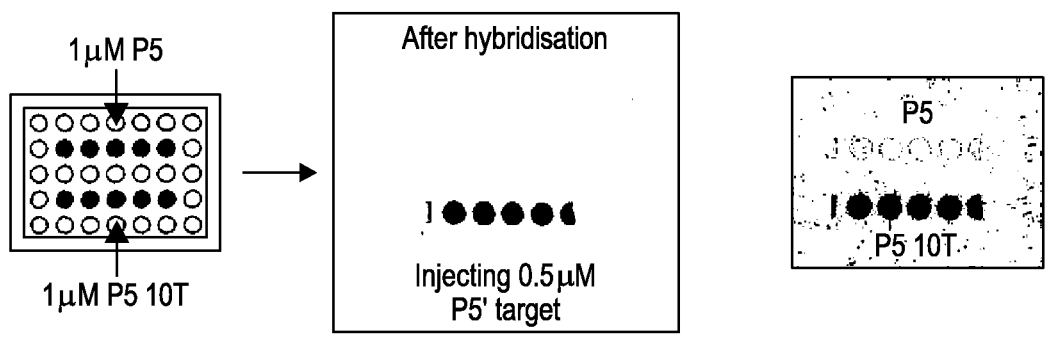
Figure 11:
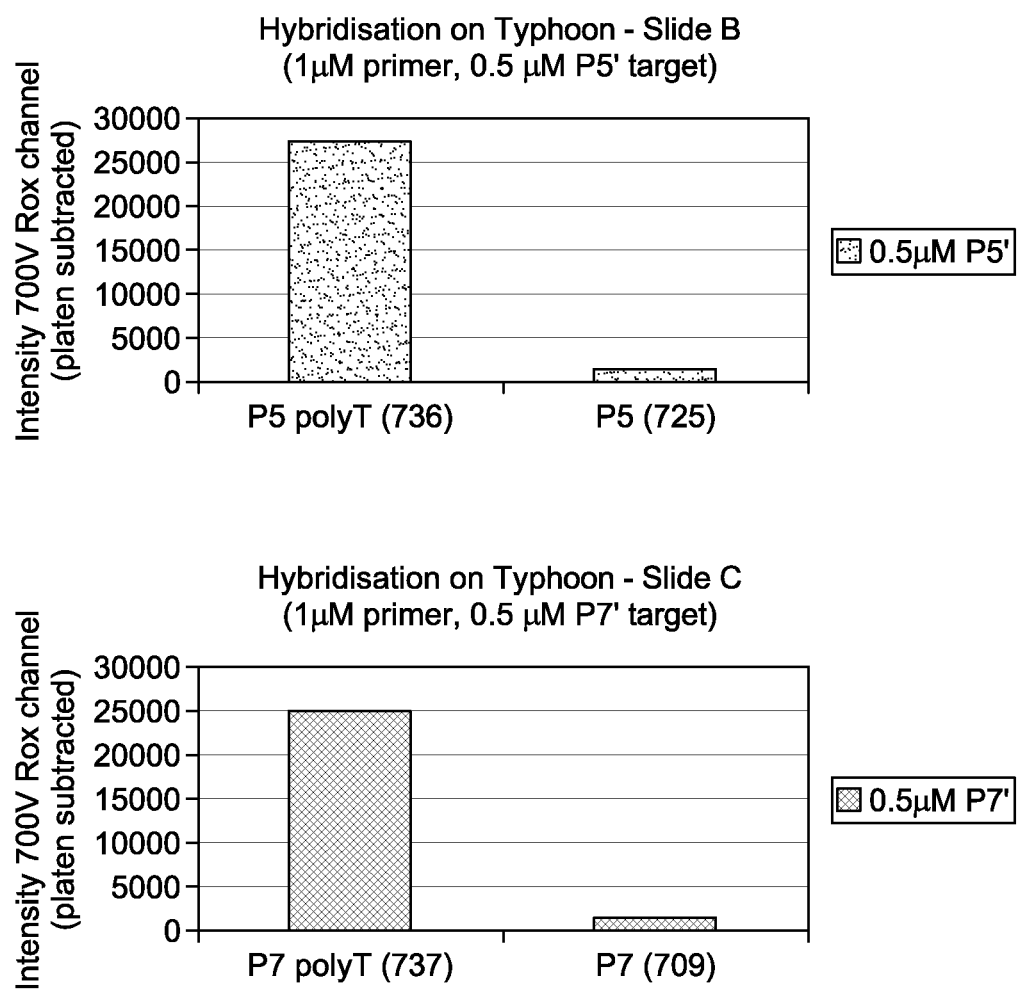
FIG. 11 graphically represents the results of typical hybridisation experiments according to Example 14.

Results: The results presented in FIGS. 10 and 11 show a clear improvement in hybridisation signal for both the P5 and P7 primer upon adding a spacer with 10 T bases. Not only is the signal much higher but the signal-to-noise (specific to nonspecific hybridisation) also improves immensely.

(3) Hybridization on Typhoon Slides—Effect of Spacer Length Coupling of Oligo Primers to SFA Surface:

The following 8 primers were coupled to the surface at 1.0 µM concentrations from 10 mM phosphate buffer pH 7:

```
1) P7 primer without polyT spacer:
                                    (SEQ ID NO: 3)
5'phosphorothioate-CAAGCAGAAGACGGCATACGA-3'

2) P7 primer with polyT spacer:
                                    (SEQ ID NO: 1)
5'phosphorothioate-TTTTTTTTTTCAAGCAGAAGACGGCATA
CGA-3'

3) P5 primer without polyT spacer:
                                    (SEQ ID NO: 4)
5'phosphorothioate-AATGATACGGCGACCACCGA-3'

4) P5 primer with polyT spacer:
                                    (SEQ ID NO: 2)
5'phosphorothioate-TTTTTTTTTTAATGATACGGCGACCACC
GA-3'

5) P5 primer with polyT spacer:
                                    (SEQ ID NO: 7)
5'phosphorothioate-TTAATGATACGGCGACCACCGA-3'

6) P5 primer with polyT spacer:
                                    (SEQ ID NO: 8)
5'phosphorothioate-TTTTTAATGATACGGCGACCACCGA-3'

7) P5 primer with polyT spacer:
                                    (SEQ ID NO: 9)
5'phosphorothioate-TTTTTTTTTTTTTTTTTTTTAATGATAC
GGCGACCACCGA-3'

8) P5 primer with C18 spacer:
                                    (SEQ ID NO: 10)
5'phosphorothioate-C18-AATGATACGGCGACCACCGA-3'
```

Coupling was carried out for 1 hour by spotting 7~1 of each oligonucleotide into one or more wells created by sticking a Grace Biolab CultureWell coverglass gasket (gasket 1, scheme 2) onto a Typhoon slide previously modified with 2% acrylamide, 2 mol % BRAPA silane-free acrylamide. During coupling the slides were kept in the dark in a humidity chamber. After coupling the slides were rinsed with 250 ml of 0.1 M phosphate buffer pH 7 from a wash bottle. Then each slide was vortexed 20 seconds in 10 mM/10 mM Tris/EDTA pH 8 buffer, then rinsed with MilliQ water and dried.

Hybridisation:

Hybridisation to the primers (FIG. 7) was carried out using the following complementary Texas Red labelled targets:

```
P5' complementary target to P5 sequence:
                                    (SEQ ID NO: 5)
5'Texas Red-TCGGTGGTCGCCGTATCATT-3'

P7' complementary target to P7 sequence:
                                    (SEQ ID NO: 11)
5'Texas Red-TCGTATGCCGTCTTCTGCTTG-3'
```

Hybridisation was carried out as above. A silicone gasket (gasket 2, FIG. 9) was attached to the primer modified slide and a clean glass slide placed on top to create a sealed chamber. Clips were used to ensure sealing. The space created by the gasket was then filled with one of the complementary targets (P5' or P7') then the primer-modified side was placed in contact with an aluminium heating block. A box was placed on top to prevent access of light. The temperature of the aluminium block was increased from room temperature to 95° C. (required 15 minutes). The temperature of the heater was then turned down to 40° C. and the slides allowed to cool to 50° C. (required 2 hours). Once at 50° C. the slide was allowed to cool to room temperature during 10 minutes. The complementary target solution was then removed with a syringe and the inside washed by injection 6× with 5×SSC, 0.1% Tween 20. The gasket, clips and slides were then dismantled and the primer-modified slide rinsed with agitation in a tube containing 5×SSC, 0.1% Tween 20 for 2 minutes. This was repeated then the primer-modified slide was rinsed with O.1×SSC, 0.1% Tween 20, twice for 2 minutes with agitation. The slide was then dried with Argon and scanned dry at 700V as above.

Figure 12A:
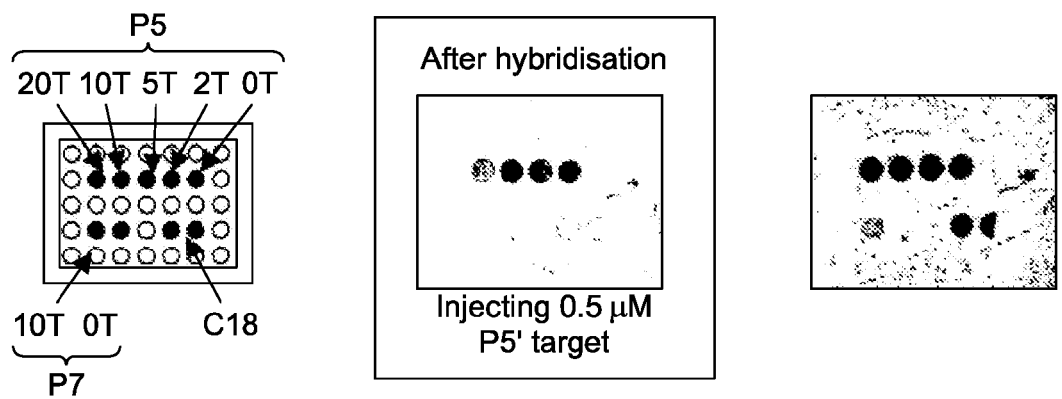
FIGS. 12(a) and 12(b) illustrate the results of hybridisation experiments using immobilised oligonucleotide primers containing varying numbers of spacer nucleotides and complementary labelled target oligonucleotides.
Figure 12B:
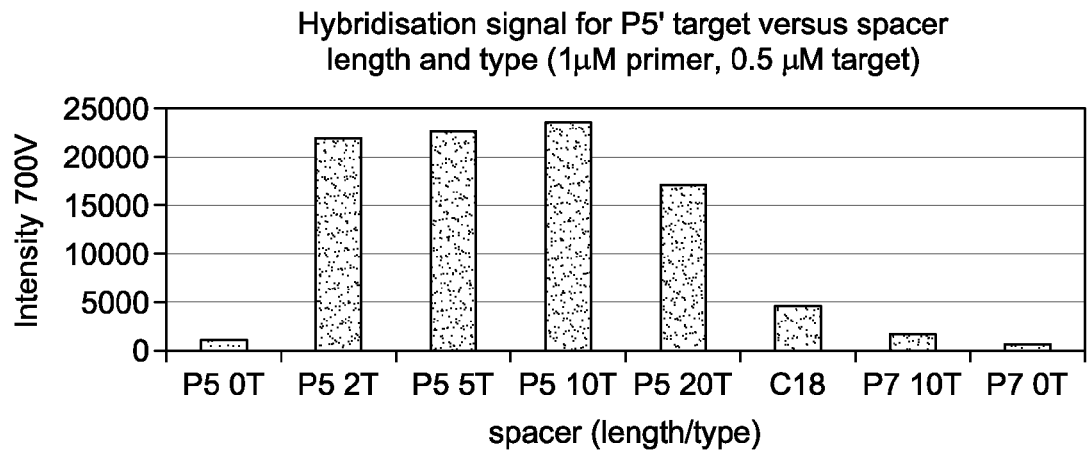
Figure 12C:
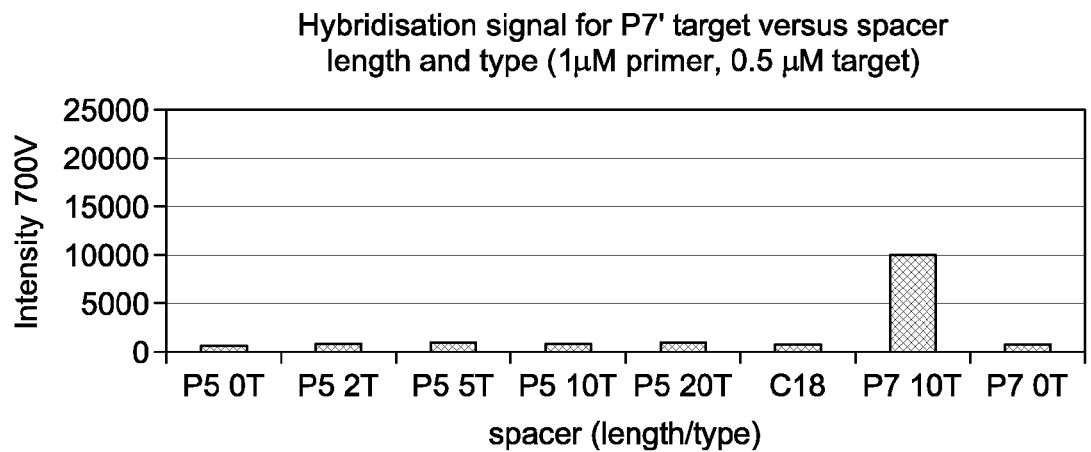
FIG. 12(c) provides a similar representation versus P7' target.

Results:

The results presented in FIG. 12 show that hybridisation yield increases sharply with polyT spacer length up to 10 Ts but between 10T and 20T bases it begins to decrease. A reduced hybridisation yield above an optimum spacer length has also been reported elsewhere (Shchepinov, M. S. et al. (1997) Nucl. Acids Res. 25, 1155-1161; Guo, Z. et al (1994) Nucl. Acids Res. 22, 5456-5465). One possible explanation could be that larger primers have lower primer density on the surface and therefore result in a smaller hybridisation signal. A C18 spacer results in only a small improvement in hybridisation yield suggesting that spacer hydrophilicity is also an important factor.

All patents, patent applications, and published references cited herein are hereby incorporated by reference in their entirety. While this invention has been particularly shown and described with references to preferred embodiments, it will be understood by those skilled in the art that various changes in form and details may be made without departing from the scope of the invention encompassed by the claims.

What is claimed is:

1. A method of localizing a target nucleic acid molecule to a solid support comprising:
   providing a solid support comprising;
      a surface;
      a plurality of nucleic acids immobilized on the surface, wherein the nucleic acids in the plurality each comprise a primer sequence selected from SEQ ID NO:3 or SEQ ID NO:4;
   providing the target nucleic acid molecule, wherein the target nucleic acid comprises a sequence that hybridizes to the primer sequence; and
   hybridizing the target nucleic acid molecule to at least one of the plurality of nucleic acids immobilized on the surface, thereby localizing the target nucleic acid molecule to a solid support.

2. The method of claim 1, further comprising:
   contacting the target nucleic acid molecule hybridized to at least one of the plurality of nucleic acids immobilized on the surface with reagents necessary to synthesize a complement of at least part of the target nucleic acid molecule, wherein the complement to at least part of the target nucleic acid molecule is covalently bound to the 3' end of at least one of the nucleic acids immobilized on the surface.

3. The method of claim 2, further comprising separating the target nucleic acid molecule from said solid support.

4. The method of claim 3, further comprising determining the sequence of the target nucleic acid molecule.

5. The method of claim 1, wherein the surface comprises a hydrogel.

6. The method of claim 5, wherein the thickness of the hydrogel is less than 100 nm.

7. The method of claim 5, wherein the hydrogel is the product of polymerizing a first comonomer with a second comonomer, wherein the first comonomer is selected from the group consisting of acrylamide, methacrylamide, hydroxyethyl methacrylate and N-vinyl pyrrolidinone, and wherein the second comonomer is a functionalized comonomer selected from the group consisting of acrylamide, acrylate, methacrylate and methacrylamide.

8. The method of claim 1, wherein the target nucleic acid molecule comprises a sequence that is reverse-complementary to the primer sequence.

9. The method of claim 1, wherein the plurality of nucleic acids is immobilized on the surface via a linkage at their 5' ends.

10. A composition comprising:
    (a) a solid support comprising a surface; and
    (b) a plurality of nucleic acids immobilized on the surface, wherein the nucleic acids in the plurality each comprise a primer sequence selected from SEQ ID NO:3 or SEQ ID NO:4.

11. The composition of claim 10, wherein the nucleic acids are covalently attached to a hydrogel immobilized on the surface.

12. The composition of claim 11, wherein of the hydrogel has a thickness less than 100 nm.

13. The composition of claim 11, wherein the hydrogel is the product of polymerizing a first comonomer with a second comonomer, wherein the first comonomer is selected from the group consisting of acrylamide, methacrylamide, hydroxyethyl methacrylate and N-vinyl pyrrolidinone, and wherein the second comonomer is a functionalized comonomer selected from the group consisting of acrylamide, acrylate, methacrylate and methacrylamide.

14. The composition of claim 10, wherein the nucleic acids in the plurality each comprise the primer sequence and a template, wherein the template comprises a nucleotide sequence that is longer than 300 nucleotides.

15. The composition of claim 10, wherein the nucleic acids in the plurality each comprise a polyT spacer 5' of the primer sequence 5', wherein the polyT spacer comprises from 2 to 10 thymine nucleotides.

16. The composition of claim 10, wherein the solid support comprises a silica-based substrate, plastic, gold, titanium dioxide or silicon.

17. The composition of claim 10, wherein the nucleic acids in the plurality are hybridized to target nucleic acids comprising a sequence that is the reverse-complement of the primer sequence.

18. The composition of claim 10, wherein the primer sequence is at the 3' end of the nucleic acids in the plurality.

19. The composition of claim 10, wherein the nucleic acids in the plurality further comprise a fluorescent label.

20. The composition of claim 19, wherein the nucleic acids in the plurality further comprise a 3' blocking group.

* * * * *

SEQUENCE LISTING

```
<160> NUMBER OF SEQ ID NOS: 11

<210> SEQ ID NO 1
<211> LENGTH: 31
<212> TYPE: DNA
<213> ORGANISM: Artificial Sequence
<220> FEATURE:
<223> OTHER INFORMATION: P7 primer with polyT spacer
<220> FEATURE:
<221> NAME/KEY: misc_feature
<222> LOCATION: 1
<223> OTHER INFORMATION: 5'phosphorothioate

<400> SEQUENCE: 1
tttttttttt caagcagaag acggcatacg a                                    31

<210> SEQ ID NO 2
<211> LENGTH: 30
<212> TYPE: DNA
<213> ORGANISM: Artificial Sequence
<220> FEATURE:
<223> OTHER INFORMATION: P5 primer with polyT spacer
<220> FEATURE:
<221> NAME/KEY: misc_feature
<222> LOCATION: 1
<223> OTHER INFORMATION: 5'phosphorothioate

<400> SEQUENCE: 2
tttttttttt aatgatacgg cgaccaccga                                      30

<210> SEQ ID NO 3
<211> LENGTH: 21
<212> TYPE: DNA
<213> ORGANISM: Artificial Sequence
<220> FEATURE:
<223> OTHER INFORMATION: P7 primer without polyT spacer
<220> FEATURE:
<221> NAME/KEY: misc_feature
<222> LOCATION: 1
<223> OTHER INFORMATION: 5'phosphorothioate

<400> SEQUENCE: 3
caagcagaag acggcatacg a                                               21

<210> SEQ ID NO 4
<211> LENGTH: 20
<212> TYPE: DNA
<213> ORGANISM: Artificial Sequence
<220> FEATURE:
<223> OTHER INFORMATION: P5 primer without polyT spacer
<220> FEATURE:
```

-continued

```
<221> NAME/KEY: misc_feature
<222> LOCATION: 1
<223> OTHER INFORMATION: 5'phosphorothioate

<400> SEQUENCE: 4
aatgatacgg cgaccaccga                                          20

<210> SEQ ID NO 5
<211> LENGTH: 20
<212> TYPE: DNA
<213> ORGANISM: Artificial Sequence
<220> FEATURE:
<223> OTHER INFORMATION: P5' complementary target to PS sequence
<220> FEATURE:
<221> NAME/KEY: misc_feature
<222> LOCATION: 1
<223> OTHER INFORMATION: 5'Texas Red

<400> SEQUENCE: 5
tcggtggtcg ccgtatcatt                                          20

<210> SEQ ID NO 6
<211> LENGTH: 26
<212> TYPE: DNA
<213> ORGANISM: Artificial Sequence
<220> FEATURE:
<223> OTHER INFORMATION: P7' complementary target to P7 sequence
<220> FEATURE:
<221> NAME/KEY: misc_feature
<222> LOCATION: 1
<223> OTHER INFORMATION: 5'Texas Red

<400> SEQUENCE: 6
tttttttttt tgccgtcttc tgcttg                                   26

<210> SEQ ID NO 7
<211> LENGTH: 22
<212> TYPE: DNA
<213> ORGANISM: Artificial Sequence
<220> FEATURE:
<223> OTHER INFORMATION: P5 primer with polyT spacer
<220> FEATURE:
<221> NAME/KEY: misc_feature
<222> LOCATION: 1
<223> OTHER INFORMATION: 5' phosphorothioate

<400> SEQUENCE: 7
ttaatgatac ggcgaccacc ga                                       22

<210> SEQ ID NO 8
<211> LENGTH: 25
<212> TYPE: DNA
<213> ORGANISM: Artificial Sequence
<220> FEATURE:
<223> OTHER INFORMATION: P5 primer with polyT spacer
<220> FEATURE:
<221> NAME/KEY: misc_feature
<222> LOCATION: 1
<223> OTHER INFORMATION: 5'phosphorothioate

<400> SEQUENCE: 8
tttttaatga tacggcgacc accga                                    25

<210> SEQ ID NO 9
<211> LENGTH: 40
<212> TYPE: DNA
<213> ORGANISM: Artificial Sequence
<220> FEATURE:
<223> OTHER INFORMATION: P5 primer with polyT spacer
```

```
<220> FEATURE:
<221> NAME/KEY: misc_feature
<222> LOCATION: 1
<223> OTHER INFORMATION: 5'phosphorothioate

<400> SEQUENCE: 9 ttttttttt ttttttttt aatgatacgg cgaccaccga                               40

<210> SEQ ID NO 10
<211> LENGTH: 20
<212> TYPE: DNA
<213> ORGANISM: Artificial Sequence
<220> FEATURE:
<223> OTHER INFORMATION: P5 primer with CIS spacer
<220> FEATURE:
<221> NAME/KEY: misc_feature
<222> LOCATION: 1
<223> OTHER INFORMATION: 5'phosphorothioate-C18

<400> SEQUENCE: 10
aatgatacgg cgaccaccga                                                   20

<210> SEQ ID NO 11
<211> LENGTH: 21
<212> TYPE: DNA
<213> ORGANISM: Artificial Sequence
<220> FEATURE:
<223> OTHER INFORMATION: P7' complementary target to P7 sequence
<220> FEATURE:
<221> NAME/KEY: misc_feature
<222> LOCATION: 1
<223> OTHER INFORMATION: 5'Texas Red

<400> SEQUENCE: 11
tcgtatgccg tcttctgctt g                                                 21
```